United States Patent
Suzuki et al.

(10) Patent No.: US 7,247,861 B2
(45) Date of Patent: Jul. 24, 2007

(54) TWO DIMENSIONAL IMAGE PRODUCTION METHOD AND SYSTEM USING SOLID-STATE IMAGE SENSING DEVICE

(75) Inventors: Masakazu Suzuki, Kyoto (JP);
Takahiro Yoshimura, Kyoto (JP);
Takeshi Hayashi, Kyoto (JP); Makoto Honjo, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 74 days.

(21) Appl. No.: 11/119,516

(22) Filed: Apr. 28, 2005

(65) Prior Publication Data
US 2005/0242380 A1 Nov. 3, 2005

(30) Foreign Application Priority Data
Apr. 30, 2004 (JP) .............................. 2004-136604

(51) Int. Cl.
*G01T 1/20* (2006.01)
(52) U.S. Cl. .................................................. 250/370.09
(58) Field of Classification Search ........... 250/370.09, 250/370.14, 370.01, 370.08
See application file for complete search history.

(56) References Cited

U.S. PATENT DOCUMENTS

| | | | | |
|---|---|---|---|---|
| 4,852,137 A | * | 7/1989 | Mackay | .................. 378/62 |
| 5,530,238 A | * | 6/1996 | Meulenbrugge et al. | . 250/208.1 |
| 5,574,284 A | * | 11/1996 | Farr | .................. 250/370.06 |
| 5,773,832 A | * | 6/1998 | Sayed et al. | ............ 250/370.09 |
| 5,818,898 A | * | 10/1998 | Tsukamoto et al. | ........ 378/98.8 |
| 6,366,636 B1 | * | 4/2002 | Kamimura et al. | ............ 378/19 |
| 6,539,076 B1 | * | 3/2003 | Shoji | .................... 378/98.8 |
| 7,016,466 B2 | * | 3/2006 | Rinaldi et al. | ............. 378/98.8 |
| 7,027,558 B2 | * | 4/2006 | Ghelmansarai et al. | ....... 378/65 |
| 7,078,693 B2 | * | 7/2006 | Nonaka | .................... 250/336.1 |
| 2002/0190215 A1 | * | 12/2002 | Tashiro et al. | ......... 250/370.11 |
| 2004/0144927 A1 | * | 7/2004 | Auner et al. | ........... 250/370.11 |
| 2006/0071174 A1 | * | 4/2006 | Spartiotis et al. | ...... 250/370.13 |

* cited by examiner

*Primary Examiner*—Albert Gagliardi
(74) *Attorney, Agent, or Firm*—Koda & Androlia

(57) ABSTRACT

A two dimensional image production method by using a solid-state image sensing device, wherein the solid-state sensing device comprises a picture element producing part where electric charges generated by way of photo-electric conversion when receiving exposure is stored as charge signals, and a dark current measuring part where a dark current is stored without receiving exposure. The method comprising the steps of: preparing and storing in advance the output ratio data for a fixed exposure time between dark current component of each pixel element or each pixel element column in the picture element producing part and that of a specified pixel element or a specified pixel element column in the dark current measuring part, and producing sequentially pixel datum removed a dark current component while performing radiography, by executing a predetermined arithmetic operation for the signals of the electric charges outputted from the picture element producing part depending on the output ratio data.

15 Claims, 19 Drawing Sheets

| k | α2 | Of |
|---|---|---|
| n | α2(n) | Of(n) |
| n−1 | α2(n−1) | Of(n−1) |
| ⋮ | ⋮ | ⋮ |
| k | α2(k) | Of(k) |
| ⋮ | ⋮ | ⋮ |
| 0 | 1 | Of(0) | picture element producing part {rows n through k} dark current measuring part {row 0} position   output ratio   offset

*Fig.3*

TWO DIMENSIONAL IMAGE PRODUCTION METHOD AND SYSTEM USING SOLID-STATE IMAGE SENSING DEVICE

FIELD OF THE INVENTION

The present invention relates to a two dimensional image production method of solid-state image sensing device and a medical digital X-ray imaging apparatus using the method and more particularly to a compensation technology for removing the dark current component in the output of solid-state image sensing device.

PRIOR ART

According to the prior X-ray imaging production apparatus in which the X-rays transmitted through an object to be examined are exposed by a solid-state image sensing device to obtain the X-ray image, in order to remove the dark current component in the output of solid-state image sensing device, the image data has been obtained by radiography of the object to be examined, thereafter radiography has been executed again while the solid-state image sensing device has not exposed X-rays, the compensation data only for the dark current component has been obtained, and the image data in which the dark current component is compensated has been obtained by the difference of the image data and the compensation data.

However, such an image producing method has had a problem such that it takes time because radiography is executed twice and further twice memory means are required in order to store the compensation data.

In order to solve the above-mentioned problems, JP-A-2000-175907 discloses that a pixel element which does not expose is prepared for the solid-state image sensing device, the dark current component per unit time is measured from the stored charge signals of the pixel element, the charge storage time of each pixel element forming an image is obtained, and the dark current of each pixel element is calculated from the obtained storage time and the dark current component per unit time to execute compensation.

However, according to the above-mentioned prior art, the dark current component included in the stored charge signals extracted through a charge transportation path of the pixel element forming an image is considered to be uniformly proportional to the charge storage time, so that scattering characteristics of each pixel element are not considered. Further according to this method, the dark current compensation is not executed at the same time of radiography, but the dark current component is subtracted after radiography, so that there has been a problem that the process time is long. In addition, the charge storage time is required to be obtained per pixel element, however, the charge storage time varies when the profile of radiography is changed. Many processes have to be executed in order to obtain the charge storage time of each pixel element per radiography, thereby requiring long time and being disadvantageous.

SUMMARY OF THE INVENTION

The present invention is proposed in order to solve the above-mentioned problems. The object of the present invention is to provide a two dimensional image production method which achieves the dark current compensation which does not need to execute radiography again under the condition that the solid-state image sensing device does not expose X-rays in order to compensate the dark current after an image data is obtained by radiography, and further not need to consider the charge storage time in case of radiography corresponding to the scattering characteristics of each pixel element of the solid-state image sensing device, and to provide a medical digital X-ray imaging apparatus using the method.

The present invention proposes a two dimensional image production method of solid-state image sensing device with the following characteristics in order to achieve the above-mentioned objects.

According to the present invention, a two dimensional image production method by using a solid-state image sensing device, wherein the solid-state sensing device comprises a picture element producing part where electric charges generated by way of photo-electric conversion when receiving exposure is stored as charge signals, and a dark current measuring part where a dark current is stored without receiving exposure comprises the steps of: preparing and storing in advance the output ratio data for a fixed exposure time between dark current component of each pixel element or each pixel element column in the picture element producing part and that of a specified pixel element or a specified pixel element column in the dark current measuring part, and producing sequentially pixel datum removed a dark current component while performing radiography, by executing a predetermined arithmetic operation for the signals of the electric charges outputted from the picture element producing part depending on the output ratio data.

Further according to the two dimensional image production method by using the solid-state image sensing device, the ratio data between the inclination of the output change of the stored charge signals of each specified pixel element or each specified pixel element column in the picture element producing part for a fixed exposure time and the inclination of the output change of a specified stored charge signal of a specified pixel element or at least one specified pixel element column in the dark current measuring part for a fixed exposure time, are prepared in advance for removing the dark current component, and a two dimensional image is produced by executing an predetermined arithmetic operation depending on the inclination ratio data.

The output ratio data for a fixed exposure time between dark current component of each pixel element or each pixel element column in the picture element producing part and that of a specified pixel element or a specified pixel element column in the dark current measuring part means the ratio data between the output intensity of the dark current component which is contained in charge signals stored on each pixel element or on each pixel element column in the picture element producing part and the output intensity of dark current which is contained in charge signals stored on a specified pixel or a specified pixel column in the dark current measuring part. Such output ratio data of dark current component becomes a parameter reflecting dispersion of inherent in a pixel element or a pixel column element of solid-state image sensing devise, therefore the dark current component contained in the charge signals stored on each pixel element or each pixel element column can be easily calculated as expected values, by measuring dark current stored on a specified pixel element or a specified pixel element column in the dark current measuring part and then applying them to the output ratio data which are prepared in advance for each pixel element or each pixel element column in the picture element producing part, during exposure, i.e. radiography.

Accordingly in such method, by using the output ratio data as mentioned above, pixel datum removed dark current component can be easily produced without executing necessary operation relating to storage time which varies depending on the exposure time.

And in the preferred another embodiment of the present invention, the ratio data between the inclination of output change of charge signals stored on each pixel element or each pixel element column in the picture element producing part for the exposure time and the inclination of output change of the charge signals stored on a specified pixel element or at least one specified pixel element column in the dark current measuring part presents the ratio of the inclination of charge signals stored in the picture element producing part for a fixed exposure time, when it is represented by a direct function, i.e. coefficient of dark current component for exposure time between the inclination of charge signals outputted stored in the dark current measuring part for a fixed storage time which depends on exposure time for the picture element producing part, when it represents by a direct function, i.e. coefficient of dark current for storage time.

Further, in addition to the output ratio data as mentioned above, the offset data for the dark current component in each pixel element or pixel element column in the picture element producing part or the offset data for a specified pixel element or a specified pixel element column in dark current measuring part, which are not dependent on the exposure time is preferably prepared, and by using such data in operation dark current component or dark current may be more perfectly removed from the charge signals stored in picture element producing part of the solid-sate image sensing device.

Still further according to the two dimensional image production method using the solid-state image sensing device, fluctuation factor data of dark current component prepared and stored in advance based on temperature are further removed when executing the arithmetic operation.

Still further according to the two dimensional image production method using the solid-state image sensing device, the solid-state image sensing device performs a panoramic radiography, a cephalometric radiography, a linear scan radiography, a dental radiography or CT radiography.

Still further according to the two dimensional image production method using the solid-state image sensing device, the solid-state image sensing device is any one of CCD sensor, MOS sensor, C-MOS sensor, or a two dimensional flat panel sensor.

Further, the present invention proposes a medical digital X-ray imaging apparatus using the above-mentioned two dimensional image production method of solid-state image sensing device as follows.

According to the present invention, a medical digital X-ray imaging apparatus comprises a solid-state image sensing device having a picture element producing part where the electric charge generated by way of photo-electric conversion for producing visible light when receiving X-rays generated from an X-ray generators is stored and a dark current measuring part where a dark current is stored without receiving X-rays; a memory for storing in advance the output ratio data for a fixed exposure time between dark current component of each pixel element or each pixel element column in the picture element producing part ant that of a specified pixel element or a specified pixel element column in the dark current measuring part; and an image processing means for sequentially producing pixel datum removed a dark current component while performing radiography, by executing a predetermined arithmetic operation for stored charge signals outputted from the picture element producing part depending on the output ratio data.

Further according to the medical digital X-ray imaging apparatus, the ratio data between the inclination of the output change of the stored charge signals of each specified pixel element or each specified pixel element column in the picture element producing part for a fixed exposure time and the inclination of the output change of a specified stored charge signal of the specified pixel element or at least one specified pixel element column in the dark current measuring part for a fixed exposure time, are prepared in advance in the memory, and the image processing means produces a two dimensional image by executing a predetermined arithmetic operation depending on the inclination ratio data.

Still further according to the medical digital X-ray imaging apparatus, fluctuation factor data of dark current component prepared and stored in advance based on temperature are further removed when executing the arithmetic operation.

Still further according to the medical digital X-ray imaging apparatus, the solid-state image sensing device performs a panoramic radiography, a cephalometric radiography, a linear scan radiography, a dental radiography or CT radiography.

Still further according to the medical digital X-ray imaging apparatus, the solid-state image sensing device is any one of CCD sensor, MOS sensor, C-MOS sensor, or a two dimensional flat panel sensor.

According to the method proposed in the present invention, the output ratio data of the dark current component of each pixel element or each pixel element column in the picture element producing part and the dark current of a specified pixel element or a specified pixel element column in the dark current measuring part, for a fixed exposure time is prepared in advance, then in producing pixel data process, a predetermined arithmetic operation is executed during radiography for all the stored charge signals outputted from the picture element producing part depending on the output ratio data to remove the dark current component, thereby addressing to the deterioration of each pixel element or pixel column element of solid-state of imaging device.

Since it is not necessary to execute operation considering the storage time, the compensation process can be easily done in the same manner when the storage time is changed according to the radiography profile to be selected.

Further, it is not necessary to execute radiography twice for dark current compensation like in the prior art, thereby achieving in real time a dark current compensation for pixel image.

According to the further proposed method of the present invention, the ratio data of the between the inclination of the output change of the stored charge signals of a specified pixel element or a specified pixel element column in the picture element producing part for a fixed exposure time and the inclination of the output change of the pixel element or at least one pixel element column in the dark current measuring part for a fixed exposure time are obtained, so that the arithmetic operation for compensation becomes easy.

According to still further proposed method of the present invention, the fluctuation factor data of dark current component which is prepared and stored in advance based on the temperature are further removed, so that the temperature data are reflected on the compensation result of dark current, thereby being more preferable.

According to still further proposed method of the present invention, the dark current compensation is executed in case of a panoramic radiography, a cephalometric radiography, a linear scan radiography, a dental radiography or CT radiography.

According to still further proposed method of the present invention, the dark current compensation is executed in case of X-ray imaging which uses any one of CCD sensor, MOS sensor, C-MOS sensor, and a two dimensional flat panel sensor.

According to the medical digital X-ray imaging apparatus proposed by the present invention, the two dimensional image producing method proposed above is used, so that the same effects can be obtained.

BRIEF DESCRIPTION OF THE DRAWINGS

FIG. 3 is a dark current compensation table.

DETAILED DESCRIPTION OF THE INVENTION

The basic principle of producing method of a two dimensional image of solid-state image sensing device is described and a medical digital X-ray imaging apparatus using the method is specifically explained hereinafter.

EMBODIMENT 1

Figure 1:
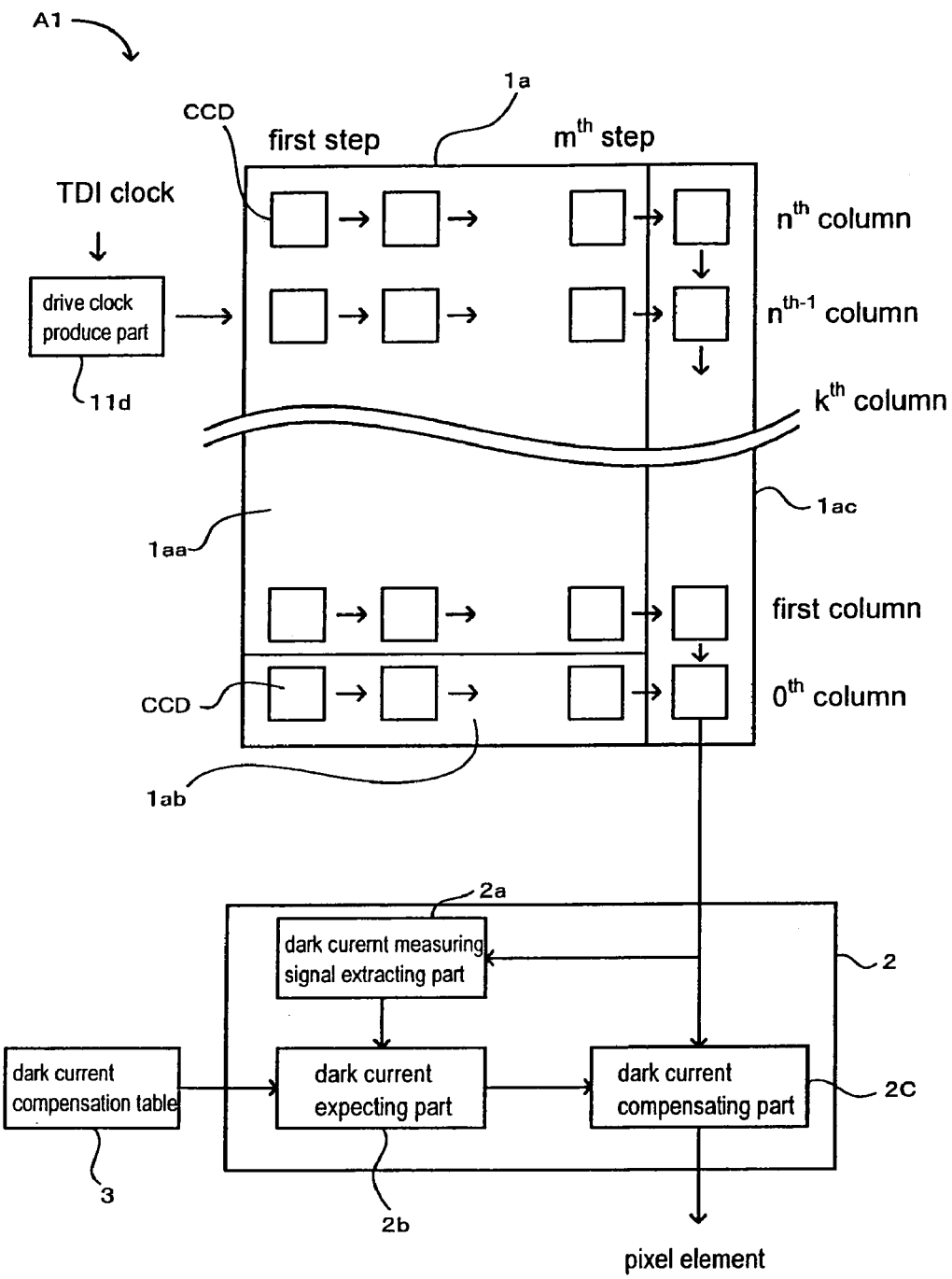
FIG. 1 is a block diagram of a two dimensional imaging apparatus showing the concept of the present invention.

FIG. 1 explains the concept of the present invention. Two dimensional image producing apparatus A1 which is comprised of only basic structural element has a solid-state image sensing device 1a, an image processing means 2, and a dark current compensation table 3 stored in a memory.

The solid-state image sensing device 1a is driven by a drive clock by an image sensing device drive circuit 11d which produces a drive clock from TDI (Time Delay Integration) clock and is divided into a picture element producing part 1aa, a dark current measuring part 1ab and a stored charge transferring part 1ac.

In the picture element producing part 1aa of the solid-state image sensing device 1a, CCD which transfers the electric charge produced by light (X-ray) with high energy is arranged in array. Also in the dark current measuring part 1ab, a single or plural columns of CCD like the picture element producing part 1aa are arranged. However, the CCD in the dark current measuring part 1ab is masked so as not to always expose light.

In the stored charge transferring part 1ac, CCD for transferring the electric charge outputted from each column in the picture element producing part 1aa and the dark current measuring part 1ab is arranged in column. The stored charge signals from the picture element producing part 1aa and the dark current measuring signals from the dark current measuring part 1ab are sequentially outputted at a fixed timing from an outlet at the lower right into the image processing means 2.

The image processing means 2 can obtain the image (pixel datum) in which the dark current component is removed from the stored charge signals taken out of the picture element producing part 1aa in case of radiography. The image processing means 2 is comprised of an extracting part of dark current measuring signals 2a for extracting the dark current measuring signals at a predetermined timing from the solid-state image sensing device 1a, a dark current expecting part 2b for expecting and calculating the dark current component in the signals of the electric charges ouputted from the picture element producing part 1aa referring to parameters, which are described later, recorded in the dark current compensation table 3 per the stored charge signals outputted from the picture element producing part 1aa and based on the dark current measuring signals outputted from the dark current measuring part 1ab, and a dark current compensating part 2c for executing a dark current compensation by subtracting an expected dark current component from the signals of the electric charges ouputted from the picture element producing part 1aa.

The dark current compensation table 3 stores parameters in advance for expecting and calculating the dark current component caused when the electric charge in each column of the picture element producing part 1aa following a predetermined transfer channel, namely a crosswise transfer channel in each column and a vertical transfer channel in the stored charge transferring part 1ac, based on the dark current measuring signals (dark current component) measured in the dark current measuring part 1ab.

Here, the principle of dark current compensation in the above-mentioned two dimensional image producing apparatus A1 is explained hereinafter.

Where the temperature at radiography is $\xi$, the electric charge accumulated in all the columns relative to each column (k=n . . . 1, 0) of the picture element producing part 1aa and the dark current measuring part 1ab of the solid-state image sensing device 1a is transferred through the stored charge transferring part 1ac, and is extracted from the apparatus A1 as stored charge signals Os(pk, $\xi$) and as the dark current measuring signals Os(P0, $\xi$), they are expressed by the following formula (I).

$$Os(pn, \xi) = Osx(pn, \xi) + Dk(pn, \xi) + Of(pn)$$
$$Os(pn-1, \xi) = Osx(pn-1, \xi) + Dk(pn-1, \xi) + Of(pn-1)$$
$$|$$
$$Os(p1, \xi) = Osx(p1, \xi) + Dk(p1, \xi) + Of(p1)$$
$$Os(p0, \xi) = Dk(p0, \xi) + Of(p0)$$

(I)

where
  Os: stored charge signal
  Osx: effective picture element signal based on exposure (signal component by the exposure of stored charge signal)
  Dk: dark current component of stored charge signal
  Of: offset component of stored charge signal
  p: position of column
  $\xi$: temperature On the other hand, when the solid-state image sensing device 1a is shielded so as not to expose, the stored charge signal Os (pk, $\xi$) and the dark current measuring signal Os (p0, $\xi$) are shown in the following formula (II) in the same manner.

$$Os(pn, \xi) = Dk(pn, \xi) + Of(pn)$$
$$Os(pn-1, \xi) = Dk(pn-1, \xi) + Of(pn-1)$$
$$|$$
$$Os(p1, \xi) = Dk(p1, \xi) + Of(p1)$$
$$= Dk(P0, \xi) + Of(p0)$$

(II)

It is known that the dark current component is substantially in ratio to the charge storage time T of the solid-state image sensing device 1a, so that the dark current component at the $k^{th}$ column is obtained by the following formula (III).

$$Dk(pk, \xi) = \alpha(pk, \xi) \cdot T$$ (III)

where
  α: coefficient
  T: storage time

When the charge storage time T is varied in several ways, the stored charge signal Os (pk, $\xi$) and the dark current measuring signal Os (p0, $\xi$) are measured, and the least square method is applied, these direct functions may be suitable. However, in a simple method, those signals are measured for two charge storage times T and a straight line passing the two points can be determined.

Further, the output ratio α2 of the dark current component Dk(pk, $\xi$) at the $k^{th}$ column of the picture element producing part 1aa and the dark current component Dk(p0, $\xi$) of the dark current measuring part 1ab for a predetermined storage time T is obtained, it is an inclination ratio of the graph of the stored charge signal Os(pk, $\xi$) and the graph of the dark current measuring signal Os (p0, $\xi$) as follows.

$$\alpha 2(pk, \xi) = Dk(pk, \xi)/Dk(p0, \xi)$$
$$= \{\alpha(pk, \xi) \cdot T\}/\{\alpha(p0, \xi) \cdot T\}$$
$$= \alpha(pk, \xi)/\alpha(p0, \xi)$$

Wherein, the output ratio α(pk, $\xi$) is supposed to be divided into the part which depends on the place pk and the temperature $\xi$, $$\alpha(pk,\xi) = \alpha 1(pk) \cdot \alpha 2(\xi)$$

Accordingly, the output ratio α2 does not depend on the temperature $\xi$ and becomes the following formula (IV).

$$\alpha 2(pk) = \alpha 1(pk)/\alpha 1(p0)$$ (IV)

According to the formulas (I) and (IV), the effective picture element signal Osx(pk, $\xi$) based on the exposure of each column (k=n . . . 1) in the picture element producing part 1aa is expressed as follows by means of the dark current measuring signal Os(p0, $\xi$) when the temperature is $\xi$ during radiography.

$$Osx(pk, \xi) = Os(pk, \xi) - Dk(pk, \xi) - Of(pk)$$
$$= Os(pk, \xi) - \alpha 2(pk) \cdot Dk(p0, \xi) - Of(pk)$$
$$= Os(pk, \xi) - \alpha 2(pk) \cdot \{Os(p0, \xi) - Of(p0)\} - Of(pk)$$

(V)

As understood from the formula (V), when the stored charge signal Os(pk,$\xi$) at each column (k=n . . . 1) in the picture element producing part 1aa is compensated during radiography by means of the dark current measuring signal Os(p0,$\xi$) of the dark current measuring part 1ab according to the formula (V), the effective picture element signal Osx(pk, $\xi$) from which the dark current component is more precisely removed based on the temperature at the time of radiography can be obtained.

Figure 2A:
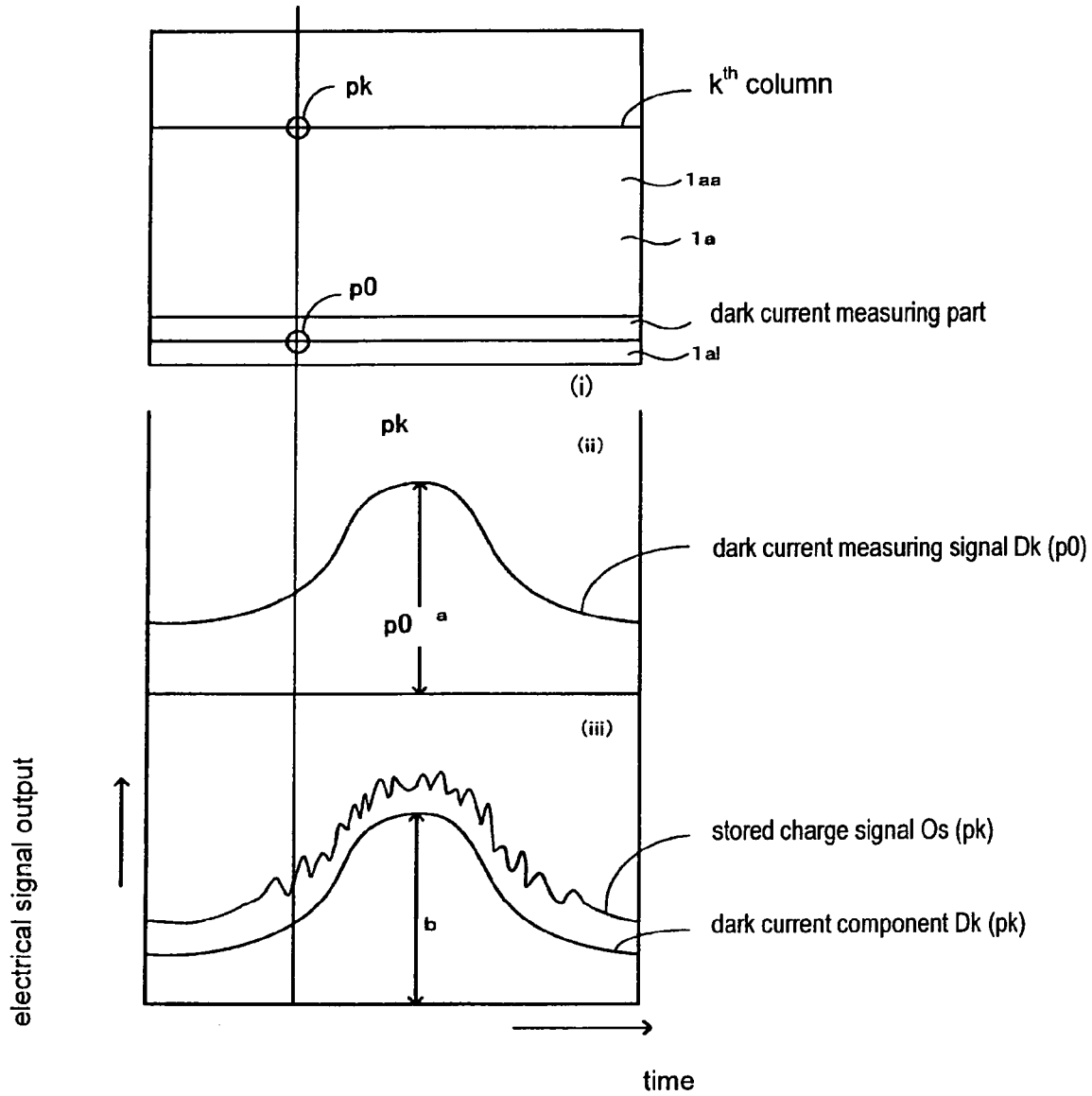
FIG. 2A is a comparison graph of the output change of a dark current component of picture element producing part and that of a dark current measuring part in case of panoramic radiography.
Figure 2B:
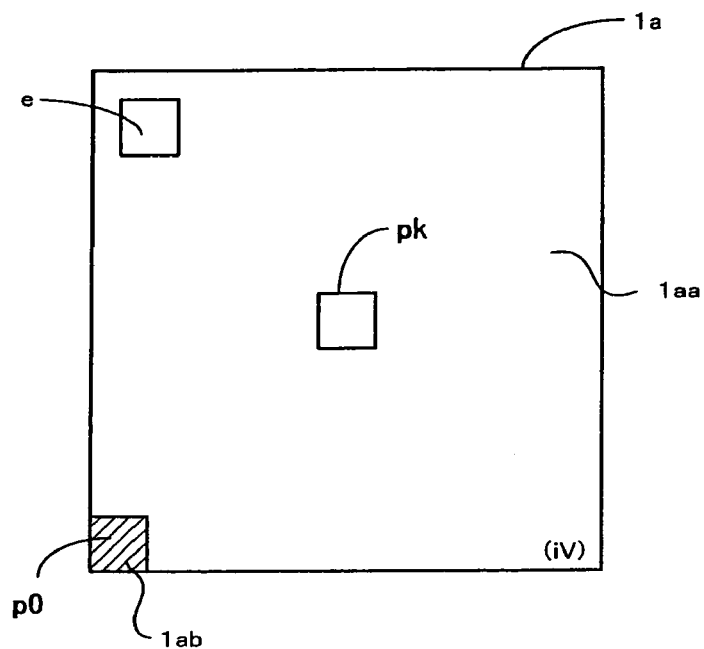
FIG. 2B is a graph showing the relation of a dark current component and an exposure time T in case of normal X-ray transparent radiography.
Figure 2B:
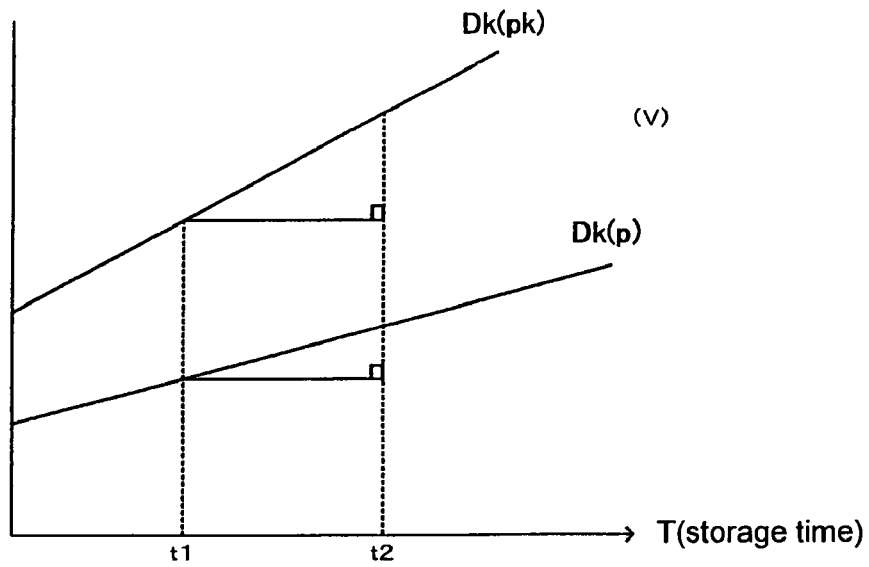

The principle of the above-mentioned dark current compensation is further explained referring to FIG. 2 in case of panoramic radiography by means of the solid-state image sensing device 1a with CCD sensor and in case of a normal X-ray transmission radiography by means of the solid-state image sensing device 1a with MOS sensor.

FIG. 2A shows the relation of the time and the electric signal output in case of a dental panoramic radiography wherein the stored charge signals (one dimensional) outputted from each column of the solid-state image sensing device 1a with CCD sensor are arranged in a time series of radiography. In the FIG. (i), the position of the $k^{th}$ column in the picture element producing part 1aa is shown with the reference pk and the position of the dark current measuring part 1ab is shown with the reference p0. The FIG. (ii) shows the dark current measuring signal (dark current component) Dk(p0) from the dark current measuring part 1ab. It shows the dark current measuring signal in the dark current measuring part 1ab when X-ray panoramic radiography is executed in advance before factory shipment. FIG. (iii) shows the stored charge signal Os(pk) from the $k^{th}$ column in case of actual radiography and the dark current component Dk(pk) therein.

As understood from the FIGS. (ii) and (iii), in case of a panoramic radiography from a cheek tooth, a front tooth, to a cheek tooth of an object to be examined, the scanning speed of panoramic radiography for the front tooth is generally reduced to increase the X-ray amount and the X-ray absorption into cervical vertebrae is compensated. In such a case the dark current component Dk(pk) corresponding to such part is increased as the scanning speed becomes slow. However, the output ratio of the dark current component in the dark current measuring part 1ab to that of the $k^{th}$ column in the picture element producing part 1aa, for a fixed exposure time is almost same, irrespective of the absolute strength variation and exposure time. Namely, the output ratio b/a is constant as shown in the figures.

Accordingly, the output ratio between the dark current component of the dark current measuring part 1ab and each pixel element or each pixel element column in the picture element producing part 1aa for a predetermined exposure time is stored in the dark current compensation table 3 in advance, the dark current component Dk(pk) can be expected and calculated by applying the output ratio for the stored charge signal Os(pk) taken out of the picture element producing part 1aa during radiography.

FIG. 2B (iv) shows the position pk of a specified pixel element and the position p0 of the dark current measuring part 1ab on the image in which the stored charge signal Os(pk) outputted from the solid-state image sensing device 1a with MOS sensor is arranged two dimensionally responsive to the position of the pixel element "e". FIG. 2b(v) is a graph showing the relation of each dark current component Dk(pk), Dk(p0) and the exposure time T.

As shown in the graph (v), the inclination ratio of the output change of the stored charge signal Dk(pk) of a specified pixel element or a specified pixel element column in the picture element producing part 1aa for the exposure time T and the output change of the stored charge signal Dk(p0) of the pixel element or at least one pixel element column in the dark current measuring part 1ab for the exposure time T is substantially constant. Therefore, when the inclination ratio of output change is stored in advance in the dark current compensation table 3 corresponding to each pixel element or each pixel element column in the picture element producing part 1aa, the output change inclination is applied to the corresponding stored charge signal Ok(pk) taken out of the picture element producing part 1aa in case of radiography and the dark current component Dk(pk) can be expected and calculated responsive to the actual radiography time.

Further, it is desirable to prepare and store the offset of stored charge signals in advance corresponding to each pixel element or each pixel element column in the picture element producing part 1aa and the dark current measuring part 1ab.

FIG. 3 shows one example of the dark current compensation table 3. In the figure, Of(pk=1 . . . n) indicates the offset value of dark current component of each column (k=1 . . . n) in the picture element producing part 1a and α2(pk=1 . . . n) indicates the output ratio α2 in a predetermined exposure time for the dark current measuring signal.

In the image processing means 2, the dark current producing part 2b refers to the dark current compensation table 3 each time the extracting part of dark current measuring signal 2a extracts dark current measuring signals Os(p0,ξ) at a predetermined timing from the signals of the electric charges ouputted from the solid-state image sensing device 1a in case of obtaining images by the solid-state image sensing device 1a. The dark current component is expected and calculated by the following formula:

$$Dk(pk,\xi) = \alpha2(pk) \cdot \{Os(p0,\xi) - Of(p0)\}$$

The dark current compensating part 2c obtains the effective picture element stored charge signal Osx(pk,ξ) in which the dark current component is removed in real time for each column (k=n . . . 1) in the picture element producing part 1aa by the following formula:

$$Osx(pk,\xi) = Os(pk,\xi) - Dk(pk,\xi) - Of(pk)$$

Next, diagrammatical procedures of producing the dark current compensation table and the dark current compensation process at the time of radiography are explained following flow charts.

Figure 4:
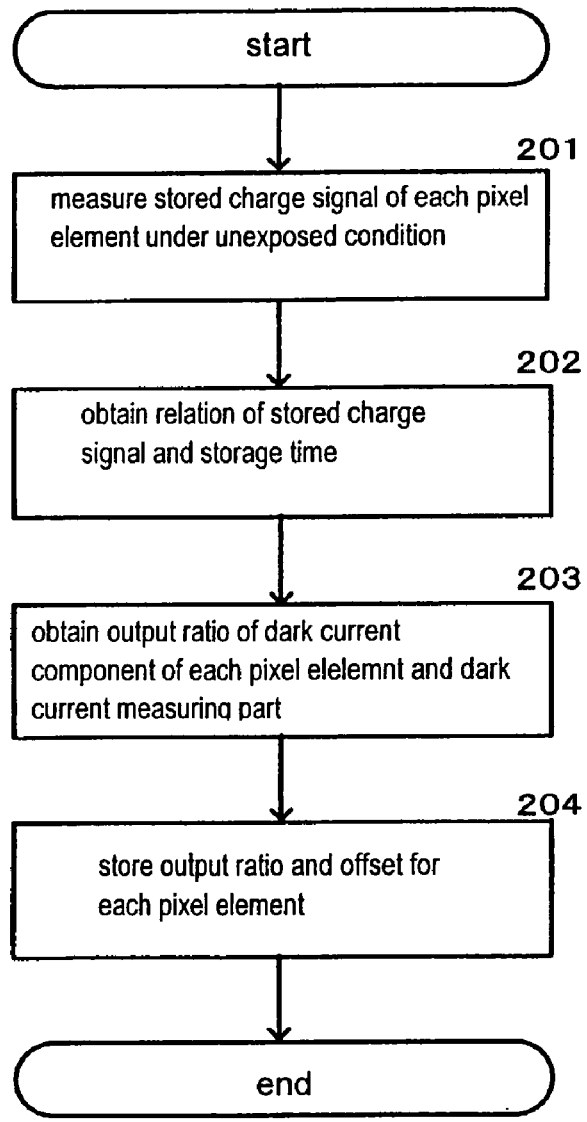
FIG. 4 is a flow chart showing procedures of producing a dark current compensation table.

FIG. 4 shows how the dark current compensation table 3 is produced before an actual radiography, for example before factory shipment. At step 201, the solid-state image sensing device 1a is entirely shielded and the stored charge signals Os (pk) for the entire pixel element including the dark current measuring part 1ab for plural storage times T are measured. At step 202, the relation of the storage time T and the stored charge signals Os(pk) for all the pixel element is obtained from the measured result. Then at step 203, the output ratio α2 of the dark current component for a predetermined exposure time of the dark current measuring part 1ab and each pixel element or each pixel element column in the picture element producing part 1aa is obtained from the obtained relation of the storage time T and the stored charge signals Os(pk) for all the pixel element. Finally at step 204, the output ratio α2 and the offset Of are stored in the dark current compensation table relative to all the pixel element. These steps are executed before shipment. The dark current compensation table 3 is stored for plural kinds of storage time in which the temperature is changed, if necessary.

Figure 5:
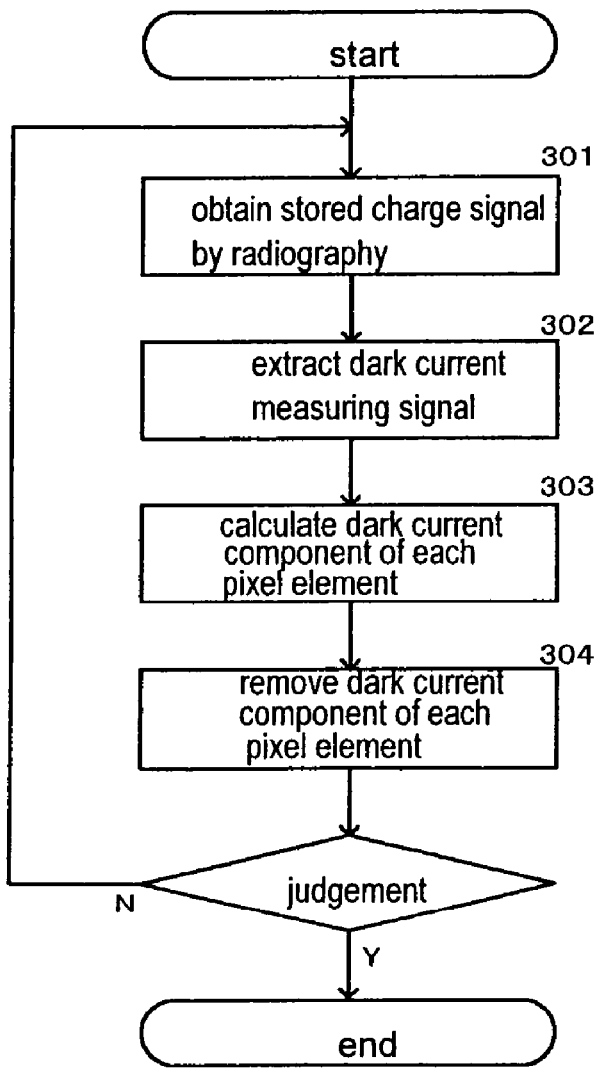
FIG. 5 is a flow chart showing compensation procedures in case of radiography.

FIG. 5 shows the compensation procedure in case of actual radiography. At step 301, radiography is executed and the stored signals Os for each pixel element are outputted. At step 302, the dark current measuring signals Os(p0) are extracted. Next at step 303, α2(pk) stored in the dark current compensation table 3 is applied to the dark current measuring signals Os(p0) to expect and calculate the dark current component Dk(pk) for all the pixel element. At step 304, the expected dark current component Dk(pk) is subtracted from the stored charge signals Os(pk) for all the pixel element for compensation. The last step 305 judges whether the process is finished, and if the procedure is not finished, the step is returned to 301.

The temperature dependency of offset Of(pk) of all the pixel element is not considered in above, however, plural sets of dark current compensation table may be prepared responsive to temperature, a suitable dark current compensation table may be selected depending on the temperature at the time of radiography, and the dark current can be compensated. In such a case, the fluctuation factor of dark current component based on the temperature which is stored in advance is further removed, thereby obtaining more preferable compensation result. In case of actual radiography, the dark current component of the exposed pixel element is expected from the relation of the exposing element and the non-exposing element at a time of radiography for the charge storage time stored in the compensation table for each pixel element in advance and from the relation of the radiography time and the pixel element of non-exposure, thereby executing the dark current compensation. For the estimation, the charge storage time at a time of pre-process and the charge storage time at a time of radiography are not used as a parameter. Therefore, the extracting process for the charge storage time is not required, thereby being applicable when a TDI clock generator is provided out of an X-ray detector.

EMBODIMENT 2

Next explained is a medical digital X-ray imaging apparatus capable of panoramic radiography in which the present invention is applied.

Figure 6:
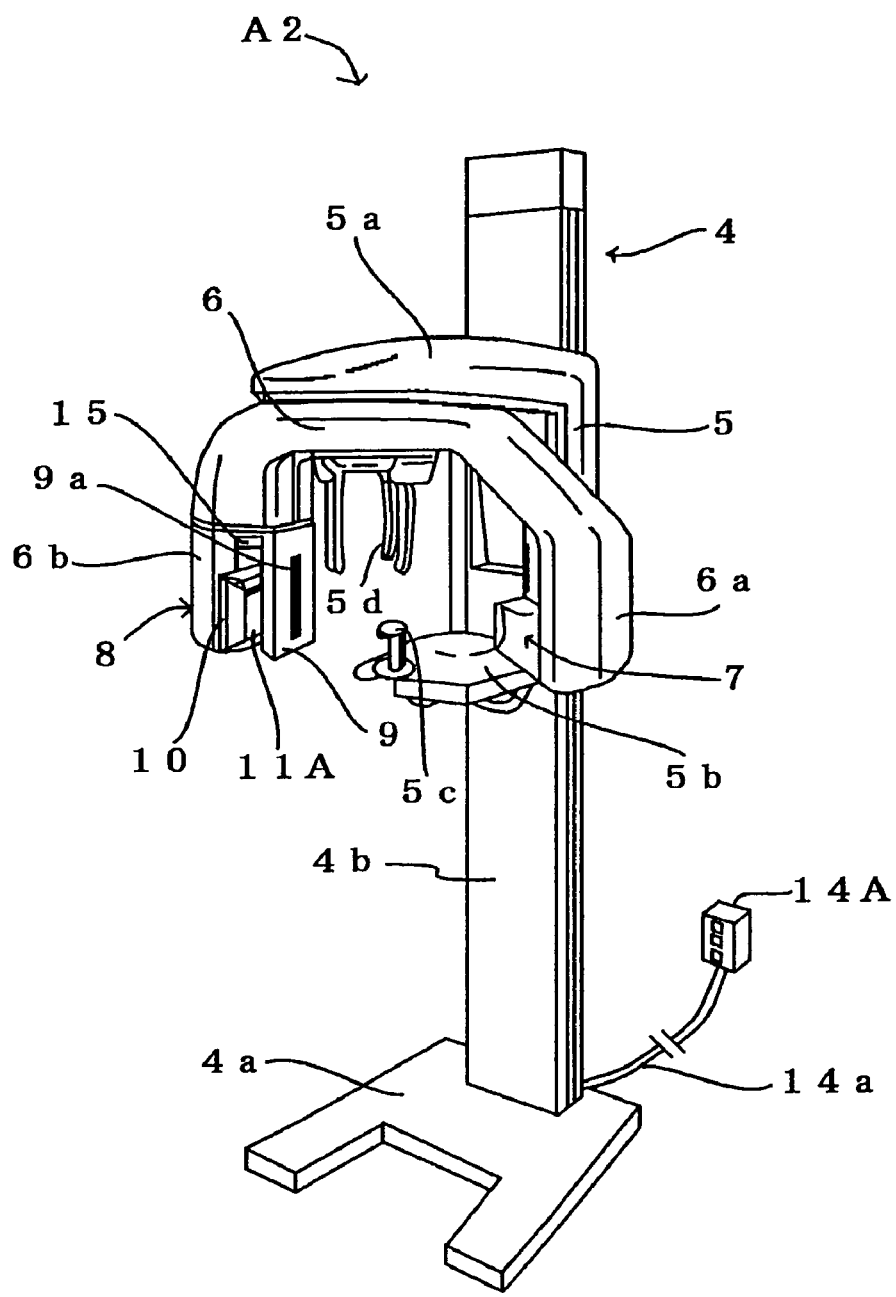
FIG. 6 is an external view of a medical digital X-ray imaging apparatus capable of panoramic radiography when the present invention is applied.

FIG. 6 shows is an external view of the X-ray imaging apparatus A2. A brace 4b stands on a base 4a of an apparatus body 4, a support body 5 is attached to the brace 4b so as to be movable up and down, and a rotary arm 6 is rotatably provided for the support body 5. A support arm 5a extending horizontally is provided for the upper end of the support body 5 and an object frame 5b is provided for the lower end thereof. A chin rest 5c is provided for the object frame 5b.

XY table which is movable in X and Y directions by means of a step motor is housed in the support arm 5a and the rotary arm 6 can be rotated while being suspended via the XY table and moving freely in the vertical plane. Head holding means 5d for object is an object holding means fixed to the lower face of the support arm 5a penetrating the rotary arm 6 and has a position control mechanism.

Turning mechanism is provided for the rotary arm 6 to turn the rotary arm 6 with respect to the support arm 5a with a step motor. The rotary arm 6 is constructed such that it turns with respective to a perpendicular axial line while moving the rotary center by means of the above-mentioned XY table. The both ends of the rotary arm 6 hangs down, an X-ray generator 7 is provided for one end 6a and an X-ray detecting part 8 is provided for the other end 6b so as to oppose each other. The X-ray generator 7 has an X-ray tube, an X-ray shielding plate with a first longitudinal slit, a control mechanism for changing the shape of the first slit, and so on (they are not shown).

The X-ray detecting part 8 has a second longitudinal slit 9a corresponding to the first slit and a shielding plate 9 with a control mechanism for the slit 9a, which are provided so as to oppose the X-ray generator 7. Detector holder 10 is provided at the back of the shielding plate 9 and a detector 11A for radiography is mounted on the detection holder 10.

Controlling part 12 for the apparatus body having a print board incorporating several circuits is provided behind the X-ray detecting part 8 and an operation panel 13 is provided so as to cover the outside thereof. Several switches and a liquid crystal display 13a are provided for the operation panel 13 (not shown).

The apparatus body 4 has a remote control box 14A connected with an operation code 14a and a main switch for turning on or off an electric source and an X-ray radiation switch are provided for the box 14A. Connector 15 is provided for the X-ray detecting part 8 for connecting to the detector for radiography.

Figure 7:
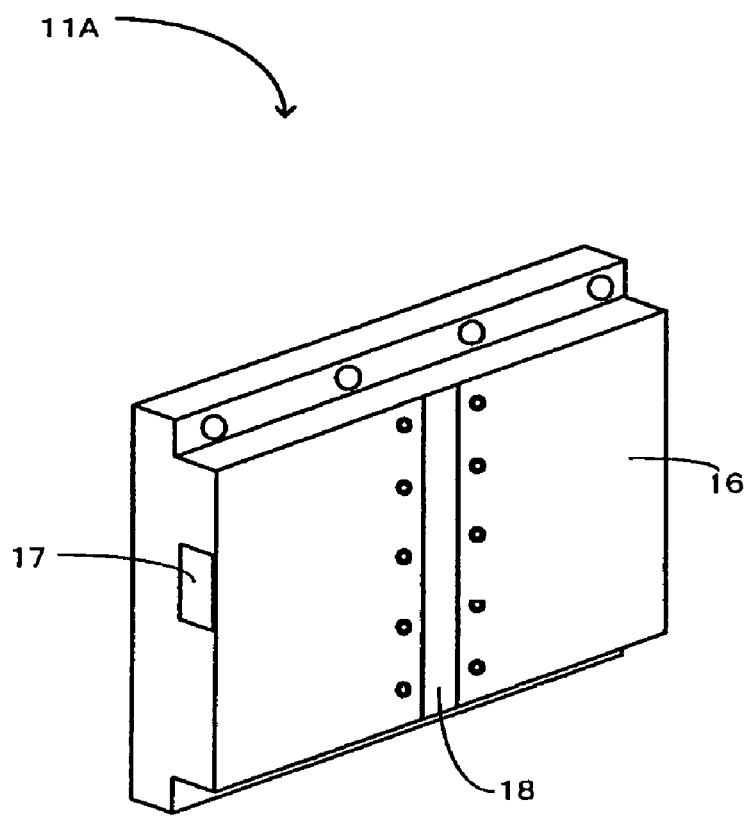
FIG. 7 is an external view of a detector for radiography which constitutes the medical digital X-ray imaging apparatus of FIG. 6.
Figure 8:
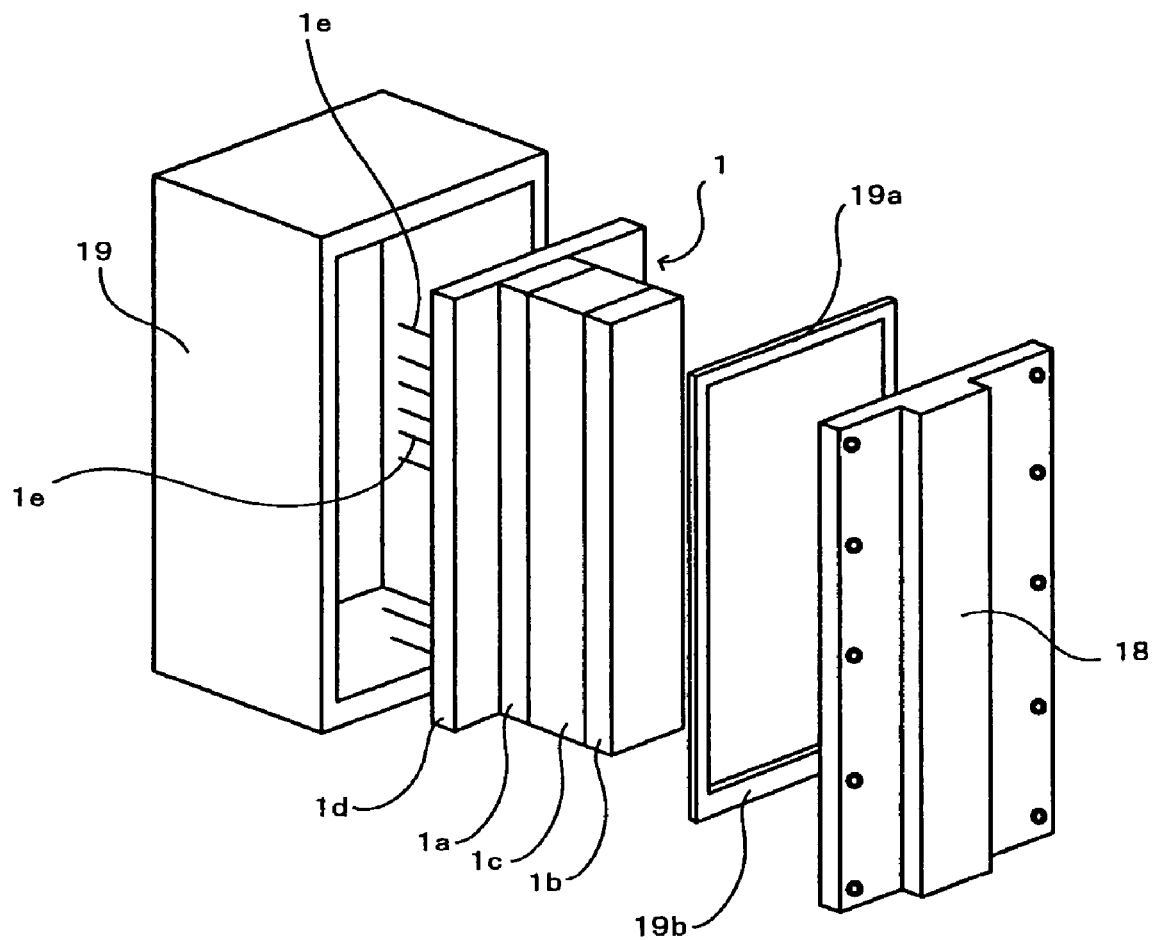
FIG. 8 explains the inner structure of the detector for radiography of FIG. 7.

FIG. 7 shows the external view of the detector 11A for radiography and FIG. 8 shows the inner structure thereof. The detector 11A includes a solid-state image sensing device unit 1 like CCD sensor and is armed with an outer housing 16 housing several kinds of circuits for the unit. Connector 17 for an outer circuit is provided on one side of the housing 16 and is generally connected with an unified cable of an electric supply line and a signal line (not shown) to the connector 15 of the X-ray detecting part 8. The connector 17 may be used for connecting to the external appliances such as a personal computer.

The outer housing 16 is made of a suitable material with necessary strength such as metal like an aluminum plate or a synthetic resin like ABS resin. X-ray receiving part 18 which is made of such material that preferably transmits X-rays but shields a visible light, for example ABS resin with dark color is longitudinally provided at the center of the front face so as to be back of the second slit 8a. The solid-state image sensing device unit 1 is provided inside of the X-ray receiving part 18.

The solid-state image sensing device unit 1 is provided on the reverse side of the X-ray receiving part 18, is comprised of a light emitting body 1b (scintillator) for converting the radiated X-rays into a visible light, an optical fiber 1c for transferring the light generated from the light emitting body 1b into the light receiving face of the solid-state image sensing device 1a, and the solid-state imaging sensing device 1a, which is explained later, and has a circuit board 1d. The reference numeral 19 indicates a protection case, 19a indicates a sealing material for shielding X-rays, and 1e is a signal pin of the solid-state image sensing device unit 1. X-ray shielding material 19b is attached at the lower part of the sealing material 19a, the X-ray shielding material 19b with a lead plate for setting the dark current measuring part 1ab, explained later, on the corresponding part of the solid-state image sensing device 1a by shielding the light emitting body 1b from X-rays.

Figure 9:
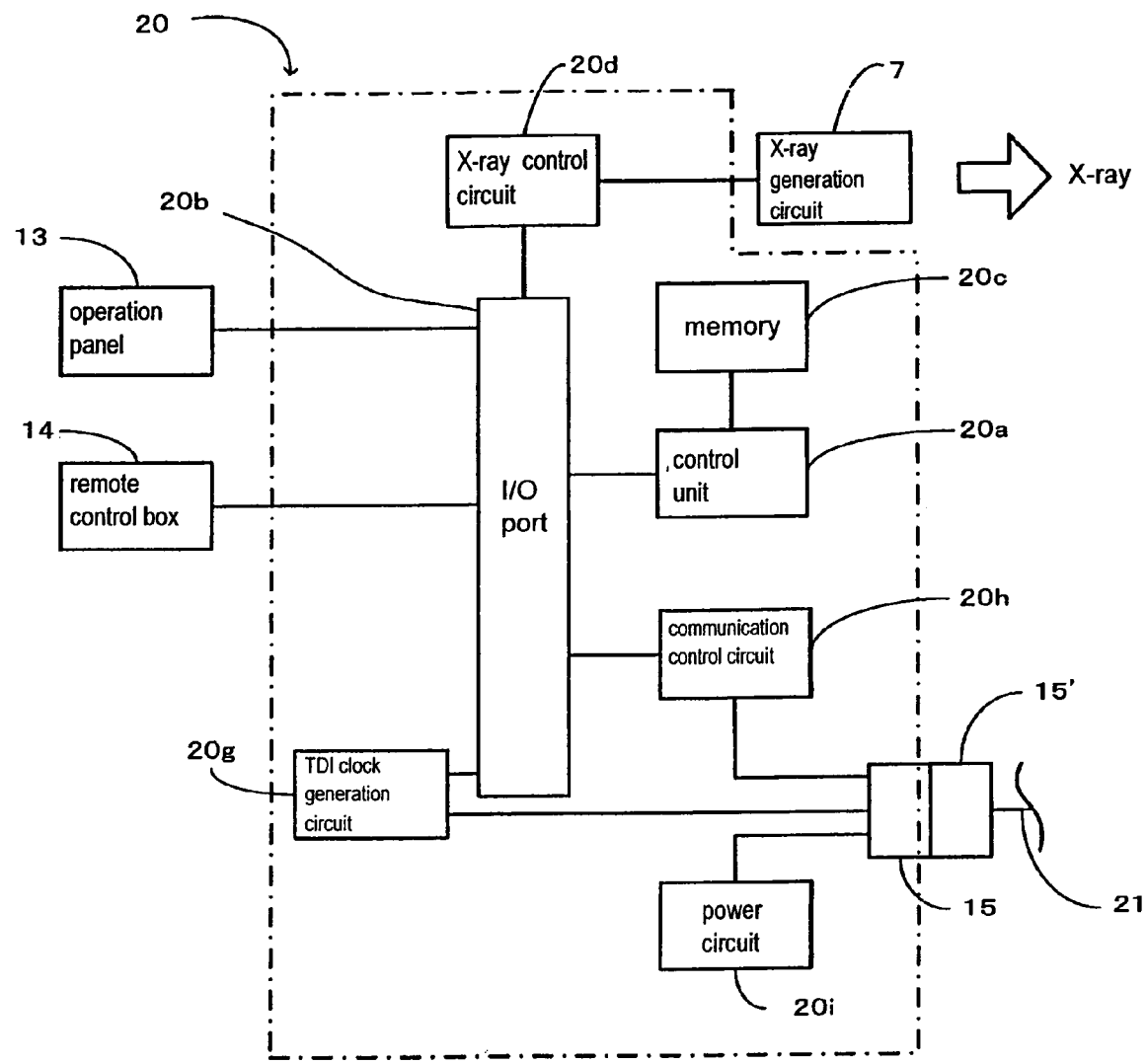
FIG. 9 is a block diagram showing the structure of a control part of a main body constituting the medical digital X-ray imaging apparatus of FIG. 6.
Figure 10:
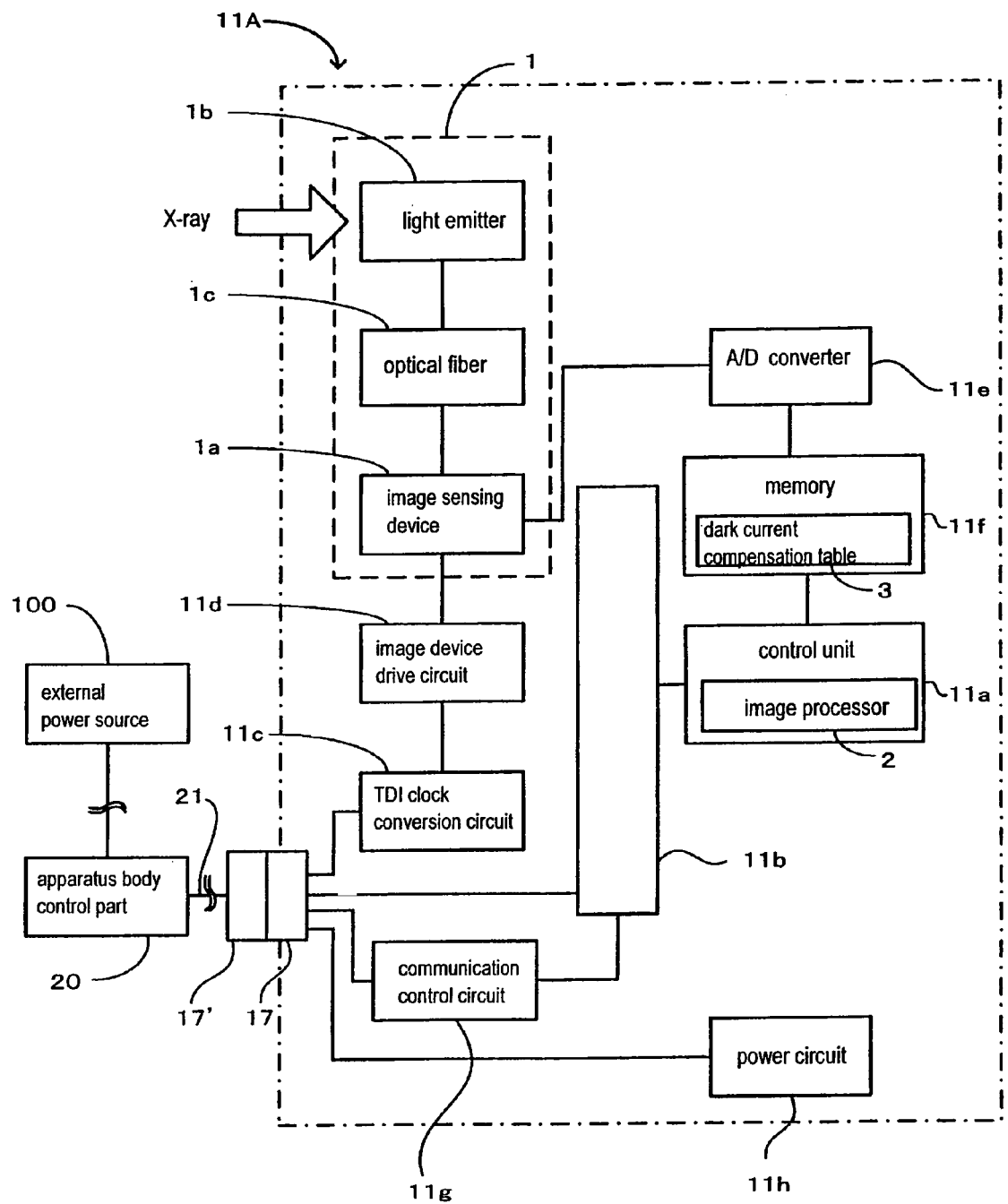
FIG. 10 is a block diagram showing the structure of a detector for radiography constituting the medical digital X-ray imaging apparatus of FIG. 6.

The diagrammatical structure of the essential part of the apparatus body 4 is explained referring to FIG. 9 and the diagrammatical structure of the essential part of the detector 11A for radiography is explained referring to FIG. 10.

FIG. 9 is a block diagram showing the diagrammatical structure of the essential part of the control part 20 of the apparatus body. The control part 20 has a control unit 20a comprised of MPU (CPU) being the center of operation and control of the entire X-ray imaging apparatus A2, an input/output port 20b and a memory 20c. In addition, it has an X-ray radiation control circuit 20d for driving and controlling the X-ray generator 7, a TDI clock generation circuit 20g, a communication control circuit 20h, and a power circuit 20i. They are connected to the control unit 20a via the input/output port 20b. Operation panel 13 for inputting several operation data or a remote control box 14 for remotely inputting the data is connected to the input/output port 20b. Further provided is a connector 15 corresponding to the connector 15' of a connection cable 21 for connecting the detector 11A for radiography and the input/output port 20b, the communication control circuit 20h and the power circuit 20i are connected to the connector 15.

FIG. 10 is a block diagram of the essential part of the detector 11A for radiography. The detector 11A has a control unit 11a comprised of MPU (CPU) for controlling the operation of each circuit in the detector 11A and the entire operation of the X-ray imaging apparatus A2 including the apparatus body 4 by itself or together with the control part 20 of the apparatus body, an input/output port 11b, a TDI clock conversion circuit 11c, an image sensing device driving circuit 11d, an A/D converter 11e, a memory 11f, a communication control circuit 11g, and a power circuit 11h. Each circuit and a connector 17 are connected as shown in the figure. The control unit 11a is constructed so as to bring out the function of the image processing means 2 for compensating dark current, which is explained as the characteristic of the present invention in Embodiment 1, by means of a software process. The dark current compensation table 3 for which the pixel element processing means refers is stored in the memory 11f in advance before factory shipment and is used for storing the effective pixel element producing a panoramic X-ray image during radiography.

The detector 11A for radiography is constructed so as to be detachable or fixedly attached to the apparatus body 4.

For the purpose, the connector 17 is electrically and regulatory connected to the control part 20 of the apparatus body by means of a connector 17' provided for the connection cable 21 introduced from the control part 20 of the main body. The control part 20 of the apparatus body is constructed such that an external appliance 100 such as a personal computer is connected so as to input control information into the control part 20 itself and the detector 11A of the radiography and to output and store the data. The memory 11f in which the dark current compensation table 3 is stored is provided in the detector 11A for radiography in the above-mentioned embodiment, however, the memory in the computer provided out of the apparatus body may be used.

Figure 11:
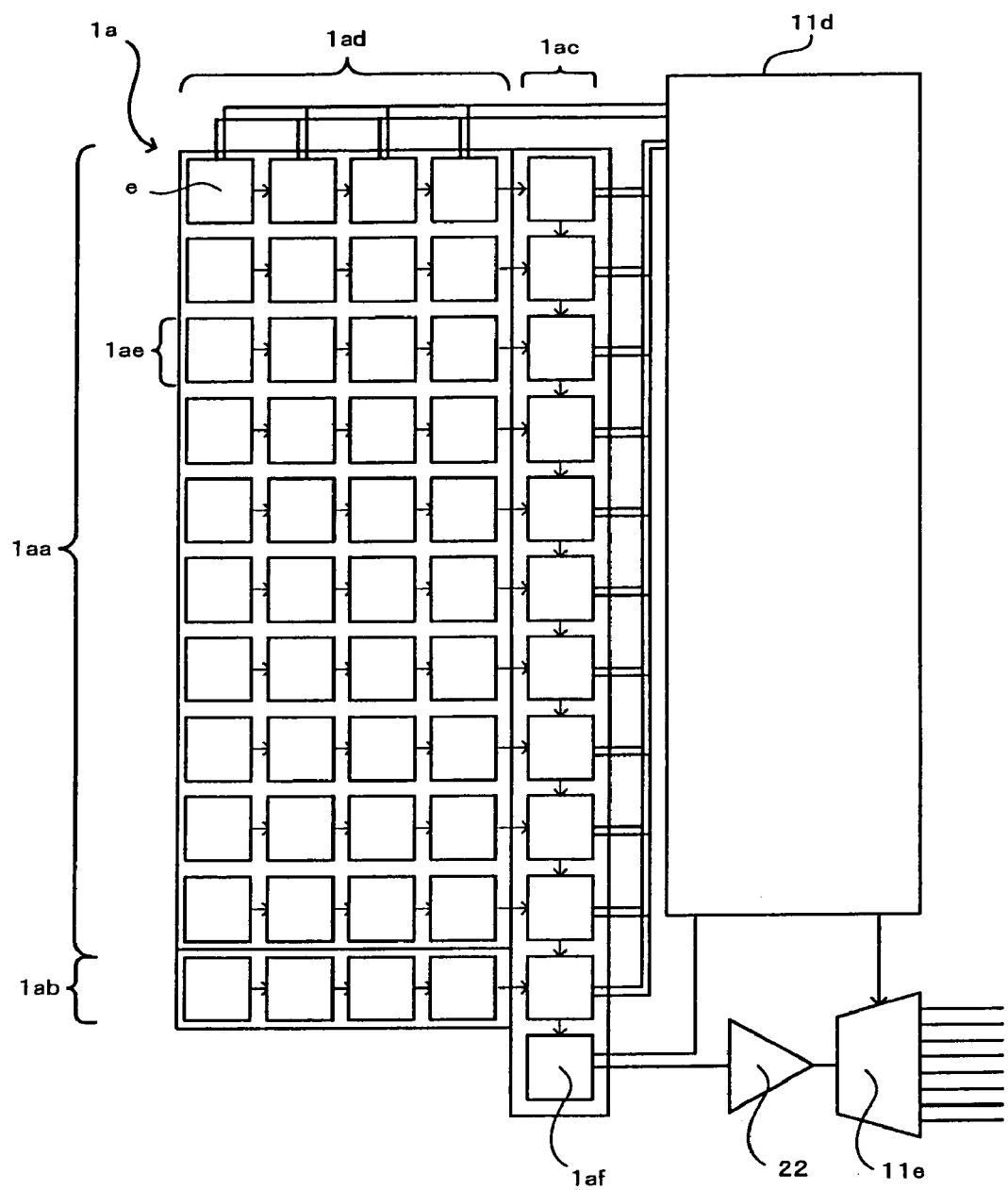
FIG. 11 shows the structure of solid-state image sensing device of FIG. 9.

FIG. 11 shows a diagrammatical structure of the solid-state image sensing device 1a provided for the detector 11A for radiography. The solid-state image sensing device 1a is comprised of CCD sensor of FFT type (Full Frame Transfer Type). The reference numeral 1ad indicates a sensor matrix consisting a light receiving part and is constructed such that a horizontal shift register 1ae for transferring the stored charge in horizontal direction is arranged in plural columns up and down and a pixel element "e" arranged in a column or step is formed by the potential well formed in the horizontal shift register part 1ae.

The reference numeral 1ac is a stored charge transferring part for forming a potential well which perpendicularly transfers the stored charge transferred in parallel in horizontal direction at once through the potential well of each horizontal shift register part 1ae which is formed in plural columns up and down, 1af indicates an output well for taking out the stored charge serially transferred in vertical direction from the stored charge transferring part 1ac, and 22 indicates an amplifier for further converting the stored charge sequentially outputted from the output well 1af into voltage signals to output as the stored charge signals.

In the sensor matrix 1ad, the pixel element "e" is arranged in 11 columns (vertical direction) and in 4 steps (horizontal direction) in the figure, however, the pixel element "e" is actually arranged in 1500 columns and 64 steps. The picture element producing part 1aa for outputting the pixel element forming the image as stored charge is allocated at the columns other than the lowest column in the figure, and the lowest column is allocated with a dark current measuring part 1ab which is always under unexposed condition by shielding X-rays with the X-ray shielding member 19b and outputs the dark current measuring signals as stored charge.

The signals of the electric charges ouputted from the amplifier 22 is sent to the AD converter 11e to be converted into digital signals. The horizontal shift register 1ae, the stored charge transferring part 1ac and the output well 1af which comprise CCD sensor transfer the stored charge following the driving clock of the imaging sensing device drive circuit 11d.

JP-A-9-200625 has disclosed such a basic operation of charge transfer of CCD sensor that the stored charge obtained by emitting light is blocked in the potential well of the sensor matrix 1ad constituting a light receiving surface to be transferred in a semiconductor material. However, the structural characteristic of the solid-state image sensing device 26c is the dark current measuring part 1ab which is always unexposed condition and outputs dark current measuring signals as stored charge is allocated to a part of the sensor matrix 1ad.

The CCD sensor which is explained above is a full frame transfer type, however, it may be FT type (Frame Transfer type). Further, a visible light from the light emitting body 1b for converting the radiated X-rays into a visible light is received in the above-mentioned embodiment, however, CCD sensor which directly detects X-rays may be used. Still further, the sensor may be a solid-state image sensing device such as MOS sensor, C-MOS sensor, a two-dimensional flat panel sensor like TFT (Thin Film Transistor), and so on in place of the above-mentioned CCD sensor.

Figures 12A, 12B:
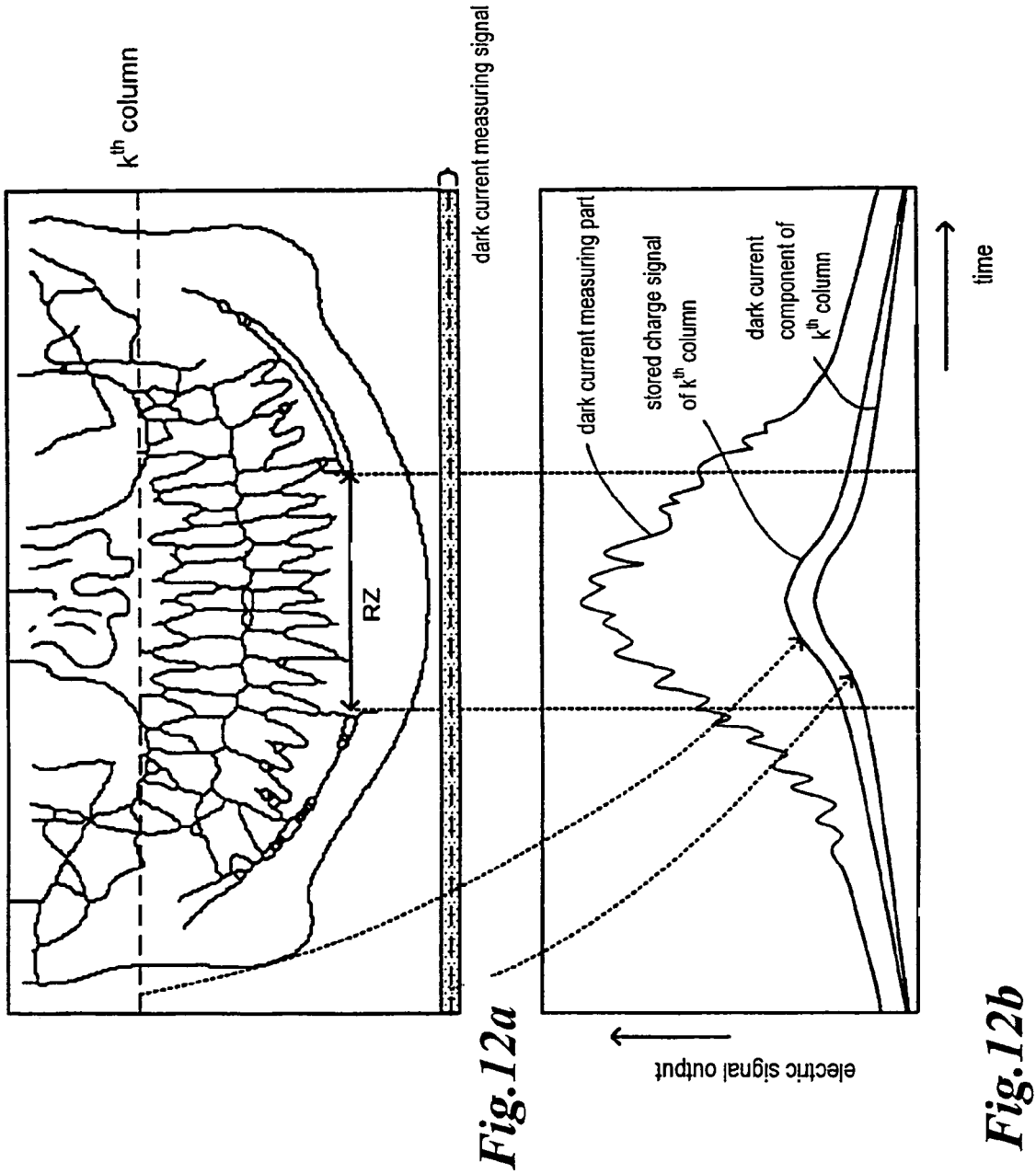
FIG. 12 is a panoramic X-ray transmitted image obtained by the medical digital X-ray imaging apparatus of FIG. 6.

FIG. 12 shows one example of a panoramic X-ray image obtained by thus constructed panoramic X-ray imaging apparatus A2, FIG. 12a is a panoramic X-ray transmitted image of the entire jaw and FIG. 12b is a graph showing the dark current component in the stored charge signals from the picture element producing part 1aa set in the solid-state image sensing device 1a and the dark current measuring signals from the dark current measuring part 26cf.

The reference RZ in FIG. 12a indicates a density compensation area generally used for panoramic radiography. X-rays are radiated for a longer time in the area in order to remove the effect of obstacle shade like cervical vertebrae and the rotary arm 6 turns slowly for the purpose. The turning speed of rotary arm 6 depends on the imaging purpose and the imaging object. Accordingly, if the TDI clock conversion circuit 11c is constructed so as to selectively generate the pattern of TDI clock signals, the X-ray imaging apparatus A2 can obtain the same panoramic X-ray transmitted image of the entire jaw, which has been obtained by moving the prior film type detector, by appropriately selecting the pattern.

As understood from FIG. 12b, the dark current component in the stored charge signals from the picture element producing part 1aa and the dark current measuring signals from the dark current measuring part 1ab have different absolute strength, however, the strengths have a proportional relation. Namely, the dark current component in the stored charge signals from the picture element producing part 1aa can be expected and calculated based on the dark current measuring signals from the dark current measuring part 1ab according to the method explained in the Embodiment 1. Further, according to the estimation and calculation, the charge storage time defined by the TDI clock is not used, so that the dark current can be easily expected and calculated in the same manner during radiography when plural patterns of TDI clock signals are prepared and one of then is selected.

CCD sensor is used as a solid-state image sensing device 1a in this embodiment, however, MOS sensor in which a photo diode of each pixel element is selected by MOS transistor and the electric charge is taken out may be used in place of CCD sensor.

Further, plural sets of dark current compensation tables 3 . . . 3 may be prepared corresponding to temperature, appropriate dark current compensation table 3 may be selected depending on the temperature at the time of radiography, and the dark current may be compensated. In such a case, the fluctuation component (fluctuation factor data) based on the temperature of dark current component which is stored in advance is further removed when the dark current component is removed, thereby obtaining a more preferable compensation result.

EMBODIMENT 3

Next explained is an embodiment wherein the present invention is applied to a medical digital X-ray imaging apparatus capable of cephalometric radiography.

Figure 13:
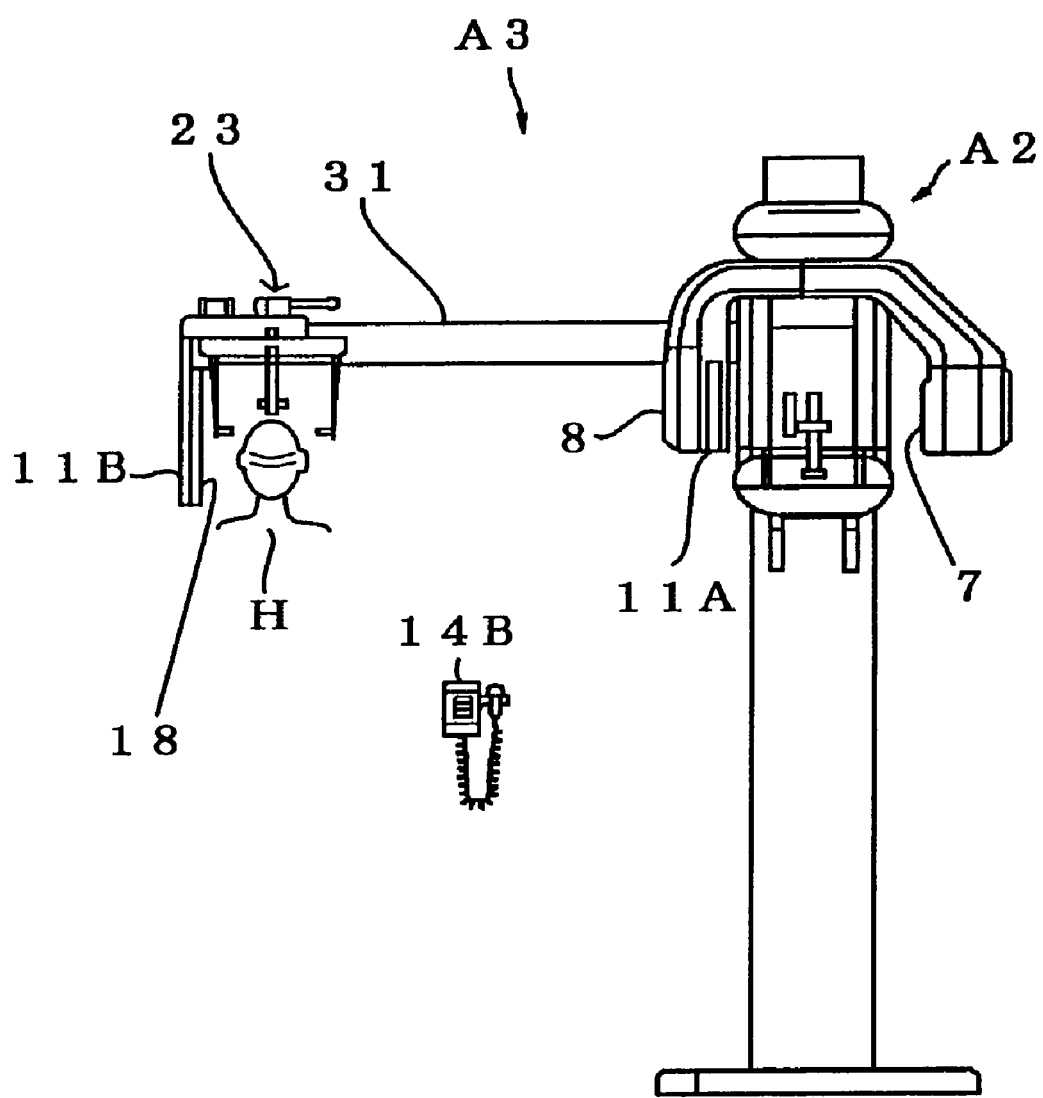
FIG. 13 is an external view of a medical digital X-ray imaging apparatus capable of a cephalometric radiography when the present invention is applied.

FIG. 13 is an external front view of the X-ray imaging apparatus A3. The X-ray imaging apparatus A3 is constructed such that the X-ray imaging apparatus A2 of FIG.

6 which is explained in Embodiment 2 is further detachably provided with a detector 11B for radiography for cephalometric radiography. In addition, a support apparatus 23 for cephalometric radiography to support a head H of an object to be examined is provided, thereby enabling a cephalometric radiography as well as a panoramic radiography.

The detector 11B for radiography has the same structure as the detector 11A for radiography which is used for the X-ray imaging apparatus A2 of the Embodiment 2. Remote control box 14B has the same structure as the remote control box 14A in FIG. 6, however, the setting position and capable operations are changed in order to be used for both a panoramic radiography and a cephalometric radiography.

In case of cephalometric radiography, like the prior art, the X-ray detecting part 8 is out of the X-ray radiation area of the X-ray generator 7, the X-rays from the X-ray generator 7 transmit the object's head H fixed with the support apparatus 23 for cephalometric radiography, and they reach the detector 11B for radiography. At this time, the detector 11B for radiography is movable up and down or right and left with respective to the support apparatus 23 for cephalometric radiography in such a manner that the X-ray receiving part 18 can receive the X-ray transmitted image of the entire object's head H.

Figure 14:
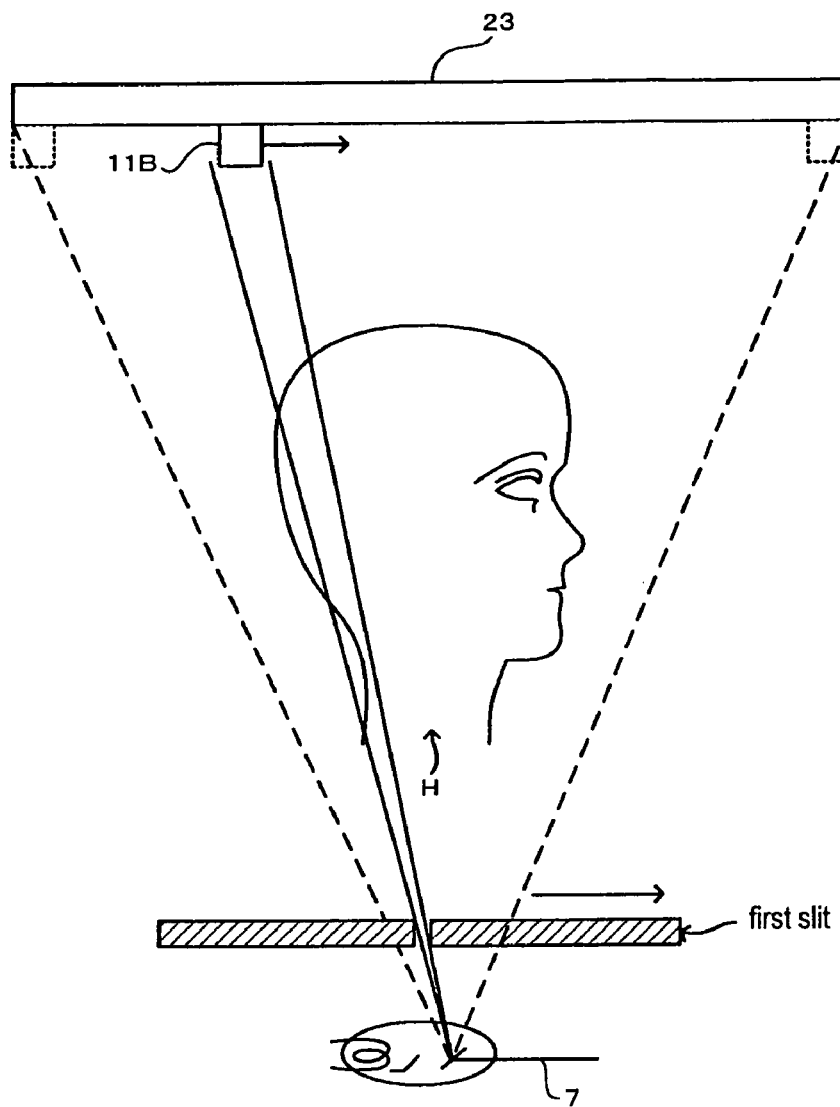
FIG. 14 shows the positional relation of an X-ray generator, an object to be examined and a detector for radiography in case of a cephalometric radiography.

FIG. 14 shows the positional relation of the X-ray generator 7, the head H of the object, and the detector 11B for radiography in case of a cephalometric radiography. As shown in the figure, the radiation area of the X-rays radiated from the X-ray generator 7 is limited into the area like a pyramid by a first slit. The first slit and the detector 11B for radiography are cooperatively moved in right and left directions in such a manner that the X-ray beam transmits the head H of the object and the X-ray transmitted image of the entire head H is received.

In case of such cephalometric radiography, the detector 11B for radiography provided for the X-ray imaging apparatus A3 has the same structure as the detector 11A for radiography provided for the X-ray imaging apparatus A2 in the Embodiment 2, so that the dark current compensation can be executed according to the method explained in the Embodiment 1.

Further, plural sets of dark current compensation tables 3 . . . 3 may be prepared corresponding to temperature, appropriate dark current compensation table 3 may be selected depending on the temperature at the time of radiography, and the dark current may be compensated. In such a case, the fluctuation component based on the temperature of dark current component which is stored in advance is further removed when the dark current component is removed, thereby obtaining a more preferable compensation result.

EMBODIMENT 4

Now explained is an embodiment wherein the present invention is applied to a medical digital X-ray imaging apparatus capable of a linear scan radiography.

Figure 15:
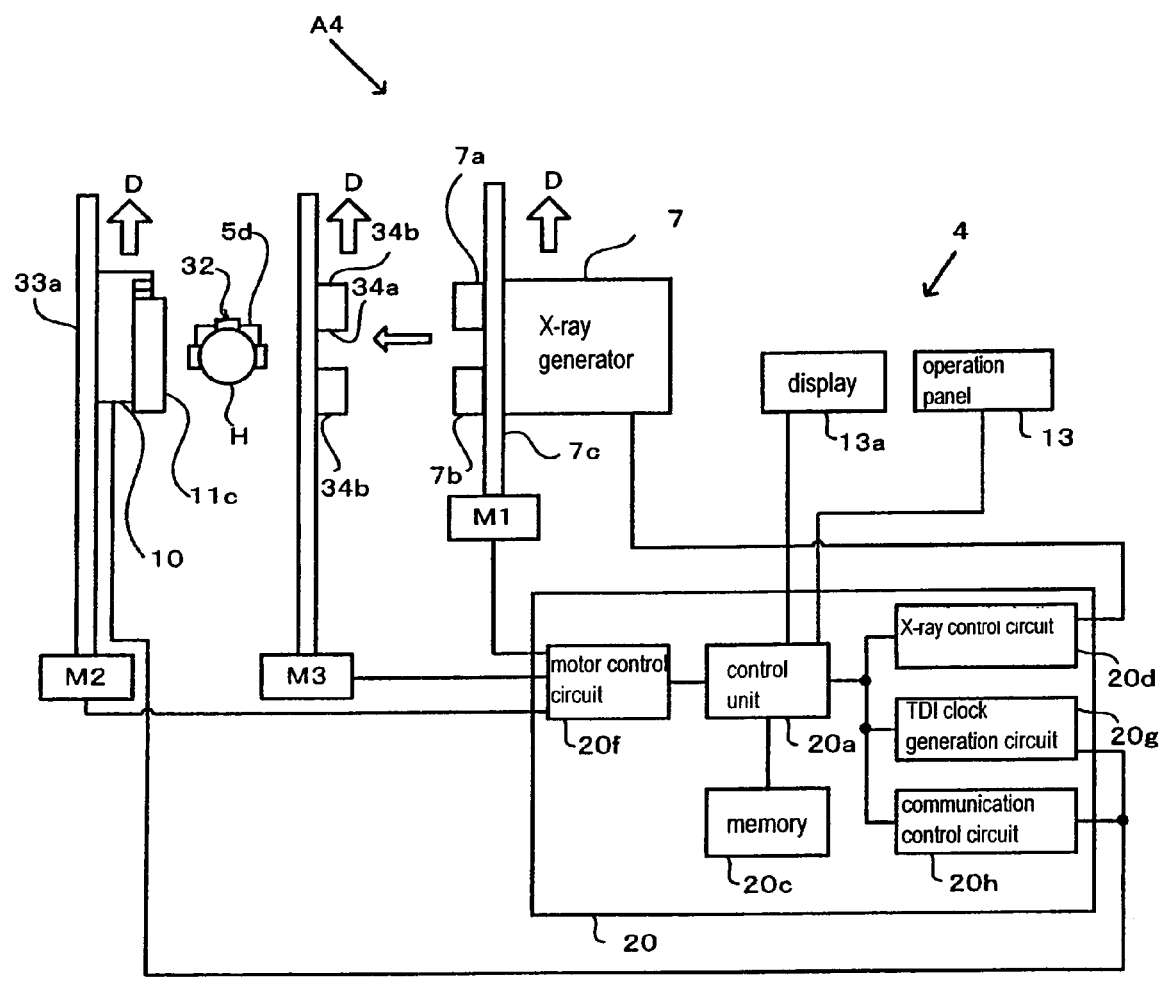
FIG. 15 is a block diagram showing the structure of a medical digital X-ray imaging apparatus capable of a linear scan radiography when the present invention is applied.

FIG. 15 is a block diagram showing the entire structure of the X-ray imaging apparatus A4. The X-ray imaging apparatus A4 is for linear scan radiography and has an X-ray generator 7, a detector 11C for radiography which receives the X-ray slit beam B generated from the X-ray generator 7 and transmitted through the object, a detector holder 10 for moving and holding the detector 11C in a detachable and speed-controllable manner, a head presser 5d (object fixing means) for fixing the object's head H to be imaged, a position detection means 32 for detecting a gradation process reference point of the object, and an apparatus body 4 for controlling the entire apparatus.

In the figure, the X-ray generator 7, the detector 11C for radiography, a support part for scanning detector, the object fixing means 5d and the position detection means 32 are shown on a flat plane when their used condition is seen from the top. The detector 11C for radiography has the same structure as the detector 11A for radiography provided for the X-ray imaging apparatus A2 in the Embodiment 2.

The X-ray generator 7 includes an X-ray tube and has a first slit member 7b made of an X-ray shielding material formed with a first slit 7a which is an opening to limit the X-ray beam widely radiated from the tube into a fixed direction and a fixed area to irradiate on a target spot, a first slit moving axis 7c for moving the first slit member 7b in the direction D shown in the figure while controlling the speed and the position, and a first slit moving motor M1 for driving the first slit moving axis 7c.

Support part 33 of detector for radiography has the detector holder 10 for detachably holding the detector 11C for radiography, a detector moving axis 33a for moving the detector holder 10 in the direction D shown in the figure so as to control the speed and the position, and a detector moving motor M2 for driving the moving axis 33a. It also has a second slit member 34b made of an X-ray shielding material which has a second slit 34a serving as an opening for passing X-rays for further limiting the X-ray slit beam B, which has been limited by the first slit 7a of the X-ray generator 7, into a fixed area before being radiated on the object's head H. It also has a second slit moving axis 34c for moving the second slit member 34b in the direction D shown in the figure so as to control the speed and the position, and a second slit moving motor M3 for driving the second slit moving axis 34c. On the other hand, the detector moving motor M2 and the second slit moving motor M3 may not be provided separately, and they may be mechanically linked by means of a timing belt so as to remove one motor.

The object's head holding means 5d (object fixing means) is constructed so as to fix the object's head H at a fixed position regardless of the movement into D direction of the detection holder 10 of the support part 33 of the detector for radiography and the second slit member 34b.

The apparatus body 4 has a control part 20 which includes a control unit 20a comprised of MPU (CPU) for achieving a central control function, a memory 20c for storing several kinds of control programs which are processed by the control unit 20a, an X-ray radiation control circuit 20d, a motor control circuit 20f, a TDI clock generation circuit 20g, and a communication control circuit 20h. The apparatus body 4 further has an operation panel 13 for receiving several operational instructions and a display means 13a for displaying X-ray images. The motor control circuit 20f is connected with the first slit moving motor M1, the detector moving motor M2, and the second slit moving motor M3 to be controlled.

According to the X-ray imaging apparatus A4, the X-ray generator 7 and the detector 11C for radiography are provided so as to interpose the object fixing means 5d as shown in the figure. When the first slit 7a, the second slit 34a and the detector 11C for radiography are synchronously moved with respect to the object's head H fixed with the head presser (head holding means) 5d, the object's head H is scanned with the X-ray slit beam B while the X-ray slit beam B radiated from the X-ray generator 7 and the detector 11C for radiography are synchronously moved into the same direction D, then the linear scan X-ray image of the object's head H is obtained. In such a case, the scanning speed (moving speed into the direction D) of X-ray slit beam B is controlled based on the stored charge signals which are the X-ray receiving data obtained by the scanning detector 11C for radiography.

When the transmitted amount is large while a hard tissue area is scanned, the radiation dosage of X-ray slit beam B which is radiated on the hard tissue area per unit time is reduced by increasing the scanning speed. On the other hand, the transmitted amount is small, the radiation dosage of X-ray slit beam B which is radiated on the hard tissue area per unit time is increased by reducing the scanning speed.

Further according to such a linear scan radiography, the detector 11C for radiography has the same construction as the detector 11A for radiography provided for the X-ray imaging apparatus A2 explained in the Embodiment 2, so that the dark current compensation can be done according to the method explained in the Embodiment 1.

Figure 16:
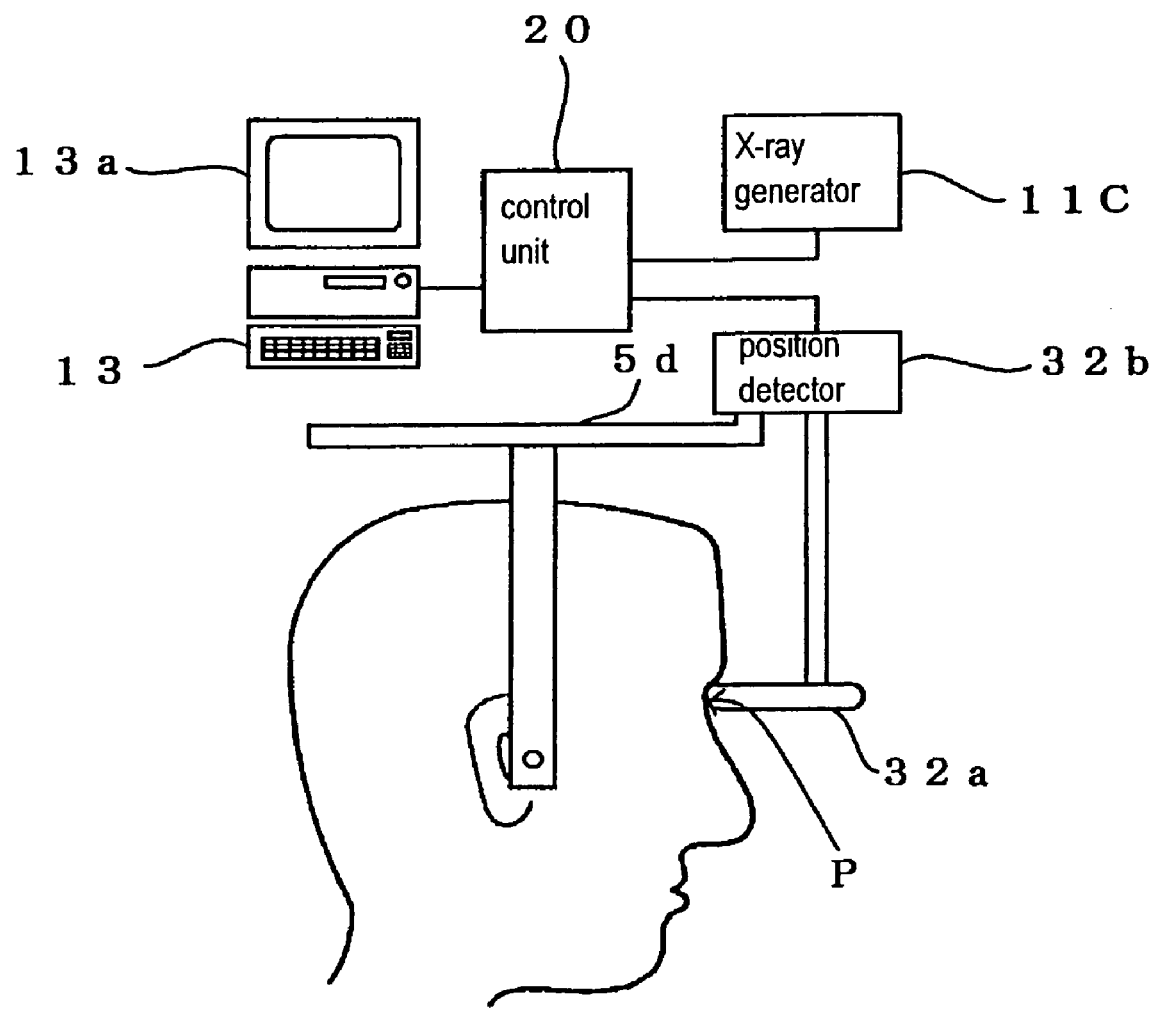
FIG. 16 shows a substantial part of a position detection means constituting the medical digital X-ray imaging apparatus of FIG. 15.

FIG. 16 is an explanatory view of the essential part of the position detection means 32 shown in FIG. 15. The position detection means 32 has a contact marker 32a and a position detector 32b which supports the contact marker 32a so as to be movable up and down and right and left shown with arrows and detects the position of the contact marker 32a which is contacted with a gradation process standard point P of the object's head H. The position detector 32b is comprised of a potentiometer fixed on the head presser 5d (object fixing means).

Such constructed position detection means 31 can easily, speedy and accurately detect the gradation process standard point P (nasion which is often used for a dental cephalometric radiography, namely a forefront of the nasofrontal suture on the median plane of human head which is important for orthodontics). Further, it is unnecessary to put a detection mark on the object. The gradation process standard point P is not limited to the position of the nasion, however, any known position may be used.

Thus obtained gradation process standard point P is used for post gradation process of a soft tissue area of a liner scan X-ray image obtained by the detector 11C for radiography or for controlling the radiation amount of X-ray slit beam B for radiography.

Further, plural sets of dark current compensation tables 3 . . . 3 may be prepared corresponding to temperature, appropriate dark current compensation table 3 may be selected depending on the temperature at the time of radiography, and the dark current may be compensated. In such a case, the fluctuation component based on the temperature of dark current component which is stored in advance is further removed when the dark current component is removed, thereby obtaining a more preferable compensation result.

EMBODIMENT 5

Now explained is an embodiment wherein the present invention is applied to a medical digital X-ray imaging apparatus capable of dental radiography.

Figure 17:
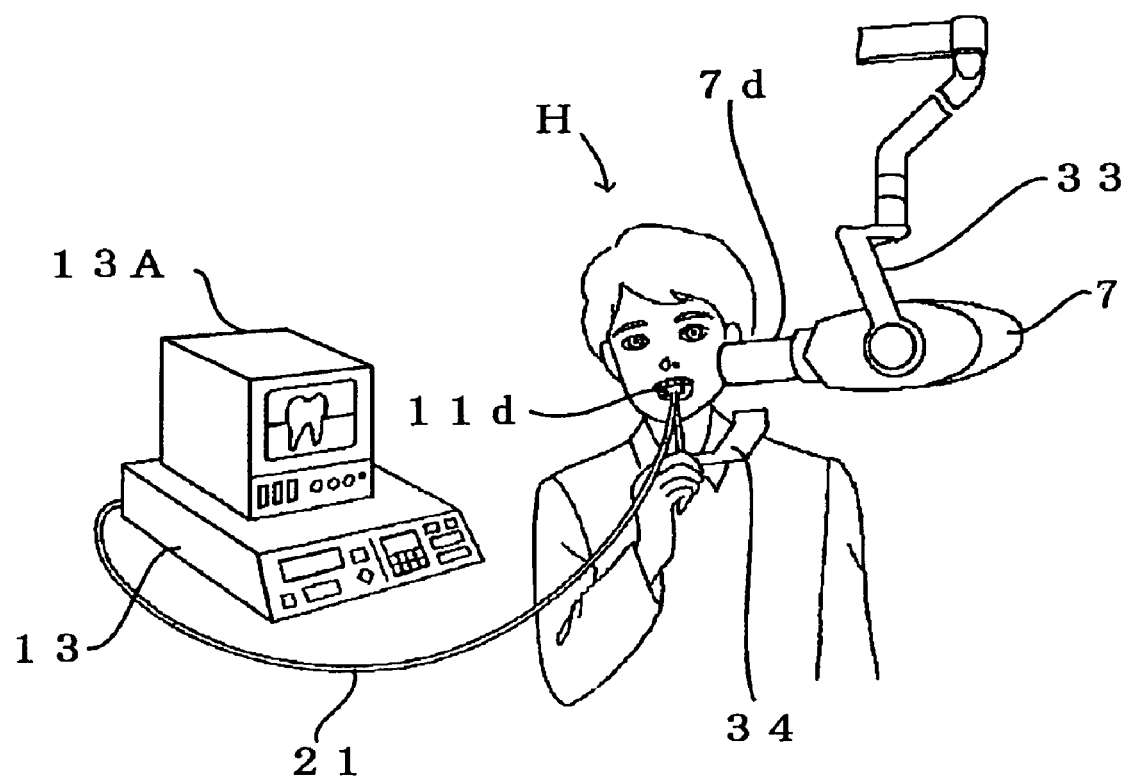
FIG. 17 shows how a medical digital X-ray imaging apparatus capable of a dental radiography is used when the present application is applied.

FIG. 17 explains how the X-ray imaging apparatus A5 is used. The object to be imaged of the X-ray imaging apparatus A5 is an intraoral area.

An X-ray generator 7 is provided so as to be able to oscillate up and down and turn horizontally with respective to a free arm 33 and the direction of an X-ray radiation tube 7d is controlled so as to irradiate X-rays into the intraoral area. A detector 11D for radiography is positioned for detecting the intensity distribution of X-rays transmitted through the intraoral area, namely for detecting the X-ray image, at a position which is opposite to the X-ray radiation tube 7d interposing the intraoral area. Namely, a positioning means 34 with the detector 11D for radiography is designed to be held by object's fingers in such a manner that the imaging plane of the detector 11D is appropriately directed into the X-ray radiating direction.

Figure 18A:
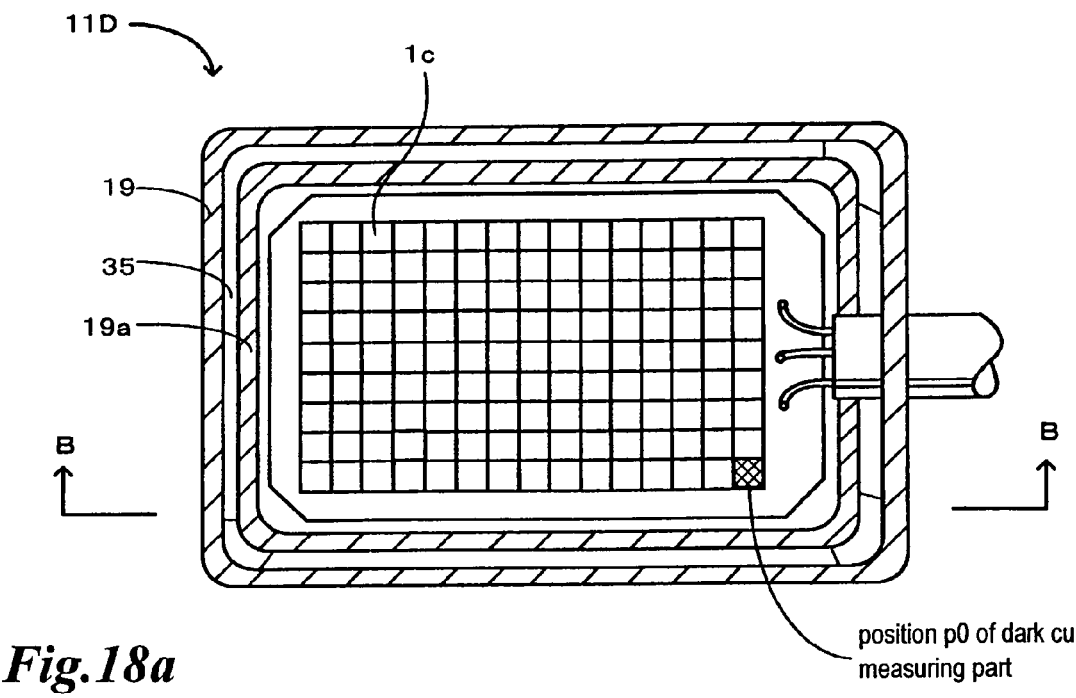
FIG. 18 is a sectional view of a detector for radiography constituting the medical digital X-ray imaging apparatus of FIG. 15.
Figure 18B:
Figure 18B:
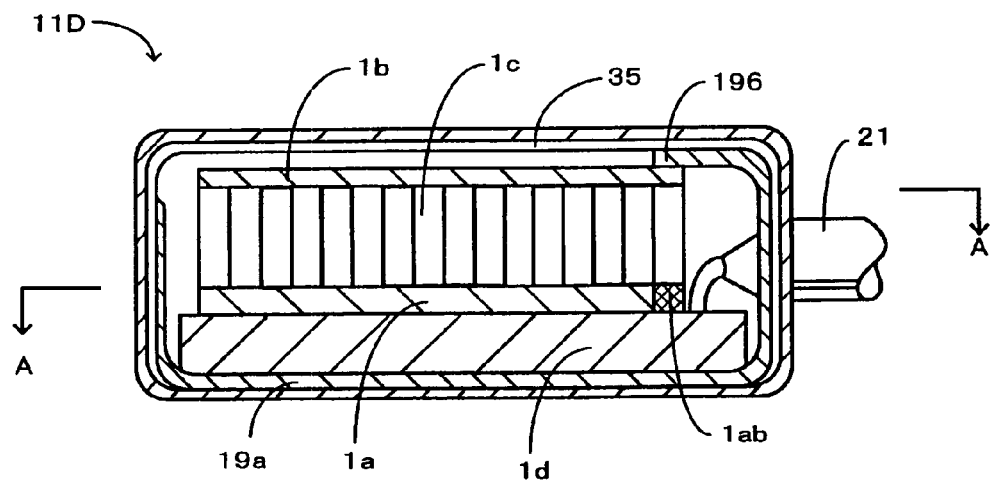

FIG. 18 is a sectional view showing the structure of the detector 11D for radiography, FIG. 18a is a horizontal section along the line A—A, and FIG. 18b is a vertical section along the line B—B.

The detector 11D for radiography is comprised of a light emitting element (scintillator) 1b for converting the radiated X-rays into a visible light, an optical fiber 1c for transmitting the emitted light from the light emitting element 1b into a light receiving surface of a solid-state image sensing device 1a, the solid-state image sensing device 1a comprised of CCD sensor for storing the electric charge generated when the fluorescence distribution transmitted by the optical fiber 1c is received and for sequentially reading out the electric charge stored for a fixed time to convert into electric signals, a board 1d made of ceramic for supporting the solid-state image sensing device 1a, and a protection case 19 for housing each structural member.

Conductive member 35 such as a thin layer of aluminum or copper is provided at the X-ray exposing face and the side of the inside of the protection case 19 so as to enclose the light emitting element 1b, the optical fiber 1c, the solid-state image sensing device 1a, and the board 1d, so that the induction noise and electrostatic serge from outside do not affect the solid-state image sensing device 1a and so on, thereby improving the anti-noise performance and the anti-serge performance. The material of conductive member 35 is preferably aluminum and beryllium with small atomic weight and the thickness is made as thin as possible like 0.01 mm to 0.1 mm, so that the X-rays entering the detector 11D for radiography do not cause attenuation and scattering.

Sealing material 19a for shielding X-rays covers at the back and side of the inside of the protection case 19 so as to prevent unnecessary scattering X-rays from entering into the back and side of the board 1d. X-ray shielding material 19b made of the sealing material 19a is provided for a part of the exposing face in the protection case 27 so as to set the dark current measuring part 1ab of the solid-state image sensing device 1a.

The board 1d has a control unit 11a (not shown) which is comprised of MPU (CPU) and has a function of image processing means 2 for dark current compensation, like the detector 11A–11C for radiography, and has a memory 11f (not shown) which previously stores the dark current compensation table 3 to which the image processing means 2 refers, like the Embodiments 2–4. Accordingly, the signals of the electric charges ouputted from the solid-state image sensing device 1a during radiography are removed its dark current component by the image processing means 2, is stored in the memory 11f as dental X-ray images, is inputted into the operation panel 13 through a cable 21, and is displayed as an image on the display means 13A.

Next, the difference between the detector 11D for radiography used for the X-ray imaging apparatus A5 and the detectors 11A-11C for radiography used in each one of the X-ray imaging apparatus in the Embodiments 2–4.

According to the detectors 11A–11C for radiography in the Embodiments 2–4, as explained referring to FIG. 11, the picture element producing part 1aa which outputs the picture element producing part 1aa forming the image as the stored charge is allocated into the columns other than the lowest column of the light receiving part 1ad of the CCD sensor, the electric charge outputted from each column is subjected to time delay integration to obtain the stored charge signals of one pixel element (stored charge signals from one dimensional image). On the other hand, the detector 11D for radiography treats the electric charge from each pixel element "e" as the stored charge signals forming a two-dimensional image.

Even when the electric charge from each pixel element "e" is treated as the stored charge signals forming a two-dimensional image, the output ratio for a fixed exposure time of the dark current measuring part and each pixel element "e" of the picture element producing part 1aa based on the dark current component taken out of the dark current measuring part 1ab is stored in the dark current compensation table 3 in advance, and the dark current component is removed by calculation applying the output ratio stored in the dark current compensation table 3 for the stored charge signals taken from each pixel element "e" during radiography. Such a method is included in the present invention.

CCD sensor is used as the solid-state image sensing device 1a in this embodiment, however, MOS sensor which is constructed so as to take out the electric charge by selecting the photo diode of each pixel element by MOS transistor may be used in place of CCD sensor.

Further, plural sets of dark current compensation tables 3 . . . 3 may be prepared corresponding to temperature, an appropriate dark current compensation table 3 may be selected depending on the temperature at the time of radiography, and the dark current may be compensated. In such a case, the fluctuation component based on the temperature of dark current component which is stored in advance is further removed when the dark current component is removed, thereby obtaining a more preferable compensation result.

EMBODIMENT 6

The present invention may be used for an X-ray CT (computer tomography) imaging apparatus other than the medical digital X-ray imaging apparatus in the above-mentioned embodiments. According to the CT apparatus, a transmission radiography is executed at plural times by changing the radiation angle on the same object and thus obtained X-ray images are processed to obtain a sectional image. Therefore, the dark current compensation of the present invention can be executed for each transmitted radiography.

The invention claimed is:

1. A two dimensional image production method by using a solid-state image sensing device, wherein the solid-state sensing device comprises a picture element producing part where electric charges generated by way of photo-electric conversion when receiving exposure is stored as charge signals, and a dark current measuring part where a dark current is stored without receiving exposure, wherein said dark current measuring part is masked, said method comprising the step of:

preparing and storing in advance the output ratio data for a fixed exposure time between dark current component of each pixel element or each pixel element column in said picture element producing part and that of a specified pixel element or a specified pixel element column in said dark current measuring part, and executing a predetermined arithmetic operation for the stored charge signals outputted from said picture element producing part depending on said output ratio data to remove said dark current component from said stored charge signals while performing radiography, thereby a two dimensional image being produced.

2. The two dimensional image production method by using the solid-state image sensing device as set forth in claim 1, wherein the ratio data between the inclination of the output change of the stored charge signals of each specified pixel element or each specified pixel element column in said picture element producing part for a fixed exposure time and the inclination of the output change of a specified stored charge signal of a specified pixel element or at least one specified pixel element column in said dark current measuring part for a fixed exposure time, are prepared in advance for removing said dark current component, and wherein a two dimensional image is produced by executing an predetermined arithmetic operation depending on said inclination ratio data.

3. The two dimensional image production method using the solid-state image sensing device as set forth in claim 2, wherein fluctuation factor data of dark current component prepared and stored in advance based on temperature are further removed when executing said arithmetic operation.

4. The two dimensional image production method using the solid-state image sensing device as set forth in any one of claims 1–3, wherein said solid-state image sensing device performs a panoramic radiography, a cephalometric radiography, a linear scan radiography, a dental radiography or CT radiography.

5. The two dimensional image production method using the solid-state image sensing device as set forth in claim 4, wherein said solid-state image sensing device is any one of CCD sensor, MOS sensor, C-MOS sensor, or a two dimensional flat panel sensor.

6. The two dimensional image production method using the solid-state image sensing device as set forth in any one of claims 1–3, wherein said solid-state image sensing device is any one of CCD sensor, MOS sensor, C-MOS sensor, or a two dimensional flat panel sensor.

7. A medical digital X-ray imaging apparatus comprising:

a solid-state image sensing device having a picture element producing part where the electric charge generated by way of photo-electric conversion for producing visible light when receiving X-rays generated from an X-ray generator is stored and a dark current measuring part where a dark current is stored without receiving X-ray; wherein said dark current measuring part is masked;

a memory for storing in advance the output ratio data for a fixed exposure time between dark current component of each pixel element or each pixel element column in said picture element producing part and that of said specified pixel element or specified pixel element column in said dark current measuring part; and an image processing means for sequentially producing pixel datum to remove a dark current component while performing radiography, by executing a predetermined arithmetic operation for stored charge signals outputted from said picture element producing part depending on said output ratio data.

8. The medical digital X-ray imaging apparatus as set forth in claim 7, wherein the ratio data between the inclination of the output change of the stored charge signals of each specified pixel element or each pixel element column in said picture element producing part for a fixed exposure time and the inclination of the output change of a specified stored charge signal of said specified pixel element or at least one specified pixel element column in said dark current measuring part for a fixed exposure time, are prepared in advance in said memory, and wherein said image processing means produces a two dimensional image by executing a predetermined arithmetic operation depending on said inclination ratio data.

9. The medical digital X-ray imaging apparatus as set forth in claim 7 or 8, wherein fluctuation factor data of dark current component prepared and stored in advance based on temperature are further removed when executing said arithmetic operation.

10. The medical digital X-ray imaging apparatus as set forth in claim 9, wherein said solid-state image sensing device performs a panoramic radiography, a cephalometric radiography, a linear scan radiography, a dental radiography or CT radiography.

11. The medical digital X-ray imaging apparatus as set forth in claim 10, wherein said solid-state image sensing device is any one of CCD sensor, MOS sensor, C-MOS sensor, or a two dimensional flat panel sensor.

12. The medical digital X-ray imaging apparatus as set forth in claim 9, wherein said solid-state image sensing device is any one of CCD sensor, MOS sensor, C-MOS sensor, or a two dimensional flat panel sensor.

13. The medical digital X-ray imaging apparatus as set forth in claim 7 or 8, wherein said solid-state image sensing device performs a panoramic radiography, a cephalometric radiography, a linear scan radiography, a dental radiography or CT radiography.

14. The medical digital X-ray imaging apparatus as set forth in claim 13, wherein said solid-state image sensing device is any one of CCD sensor, MOS sensor, C-MOS sensor, or a two dimensional flat panel sensor.

15. The medical digital X-ray imaging apparatus as set forth in claim 7 or 8, wherein said solid-state image sensing device is any one of CCD sensor, MOS sensor, C-MOS sensor, or a two dimensional flat panel sensor.

* * * * *